United States Patent [19]
Heath

[11] Patent Number: 4,834,103
[45] Date of Patent: May 30, 1989

[54] DISPOSABLE PHYSIOLOGICAL ELECTRODE SET

[75] Inventor: Roger L. Heath, Evanston, Ill.

[73] Assignee: DaRox Corporation, Niles, Ill.

[21] Appl. No.: 150,519

[22] Filed: Feb. 9, 1988

Related U.S. Application Data

[60] Continuation of Ser. No. 946,168, Dec. 22, 1986, abandoned, which is a continuation of Ser. No. 840,987, Mar. 14, 1986, abandoned, which is a continuation of Ser. No. 712,919, Mar. 18, 1985, abandoned, which is a continuation of Ser. No. 476,207, Mar. 19, 1983, abandoned, which is a division of Ser. No. 176,270, Aug. 8, 1980, Pat. No. 4,419,998.

[51] Int. Cl.$^4$ .............................................. A61N 1/04
[52] U.S. Cl. ................................................... 128/798
[58] Field of Search .............................. 128/639–641, 128/696, 798, 803

[56] References Cited

U.S. PATENT DOCUMENTS

| | | | |
|---|---|---|---|
| 1,662,446 | 3/1928 | Wappler | 128/798 |
| 3,606,881 | 9/1971 | Woodson | 128/640 |
| 3,631,851 | 1/1972 | Hesen | 128/696 |

OTHER PUBLICATIONS

Geddes et al., "Principles of Applied Biomedical Instrumentation" John Wiley and Sons, Inc., N.Y. 1968, p. 212, copy in 128/639.

Primary Examiner—William E. Kamm
Assistant Examiner—David Shay
Attorney, Agent, or Firm—Haight & Hofeldt

[57] ABSTRACT

A disposable electrode set is provided in which a single pair of electrodes have the capability of transmitting signals for monitoring, stimulating and therapeutic applications. The electrodes have a metal-metal chloride (preferably tin-stannous chloride) structure to give suitable signals for monitoring, while also providing for the transfer of high energy stimulating and therapeutic signals. Transfer of the stimulating and therapeutic signals requires that the electrodes be formed with a suitable size and shape to accommodate the high energy signals. Each of the electrodes is connected to a plug, which is a part of the disposable set, by a suitable conducting line. The plug is standarized so that the disposable set can be connected to any one or any combination of the monitoring, stimulating and therapeutic devices. The plug is especially designed so that it can be used for any of the devices, while providing a cord fault test to verify engagement of the plug with its associated connector for use in connection with a therapeutic device. Capacitive coupling for the therapeutic device can be included in the plug, if desired.

7 Claims, 9 Drawing Sheets

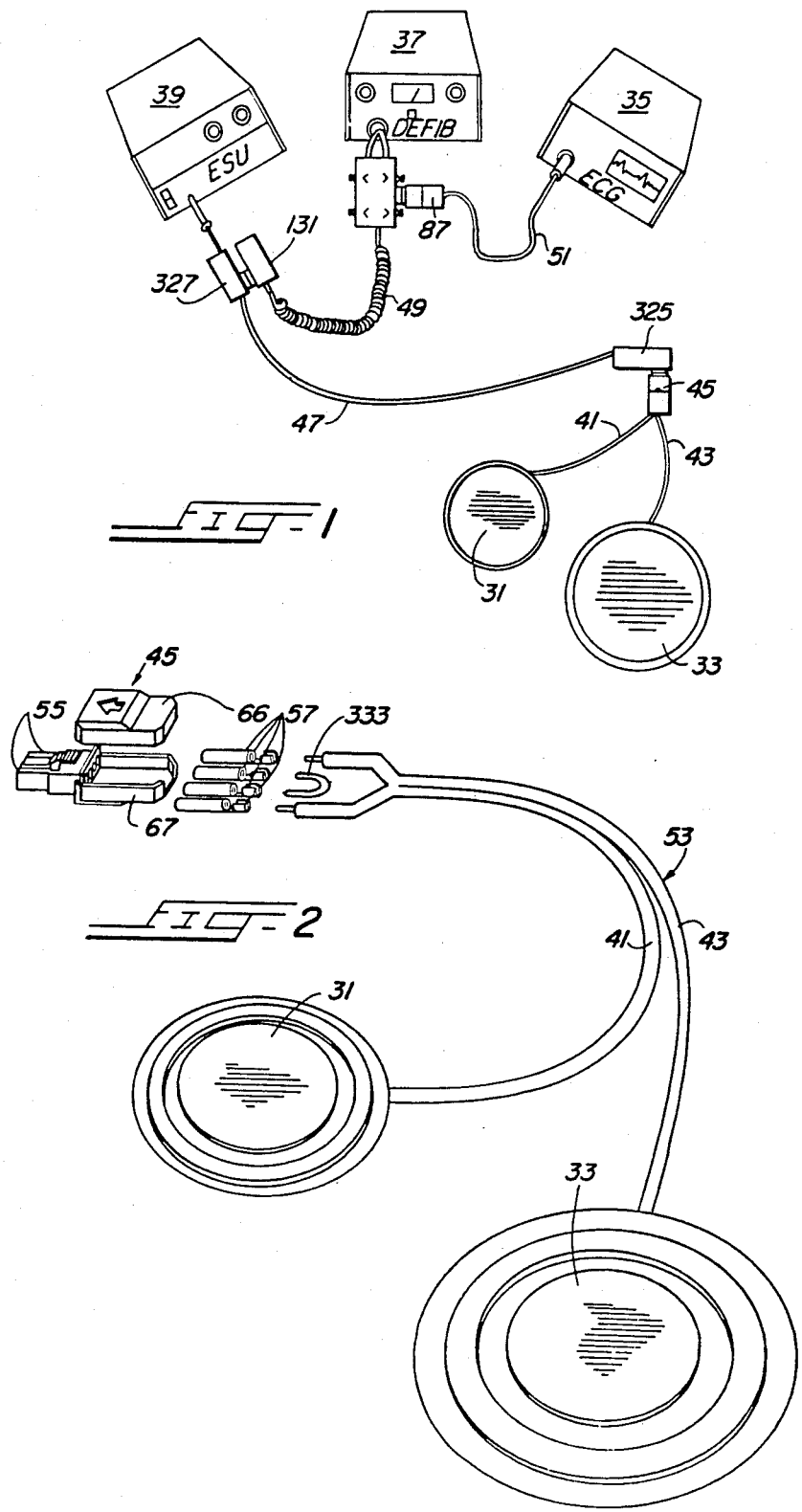

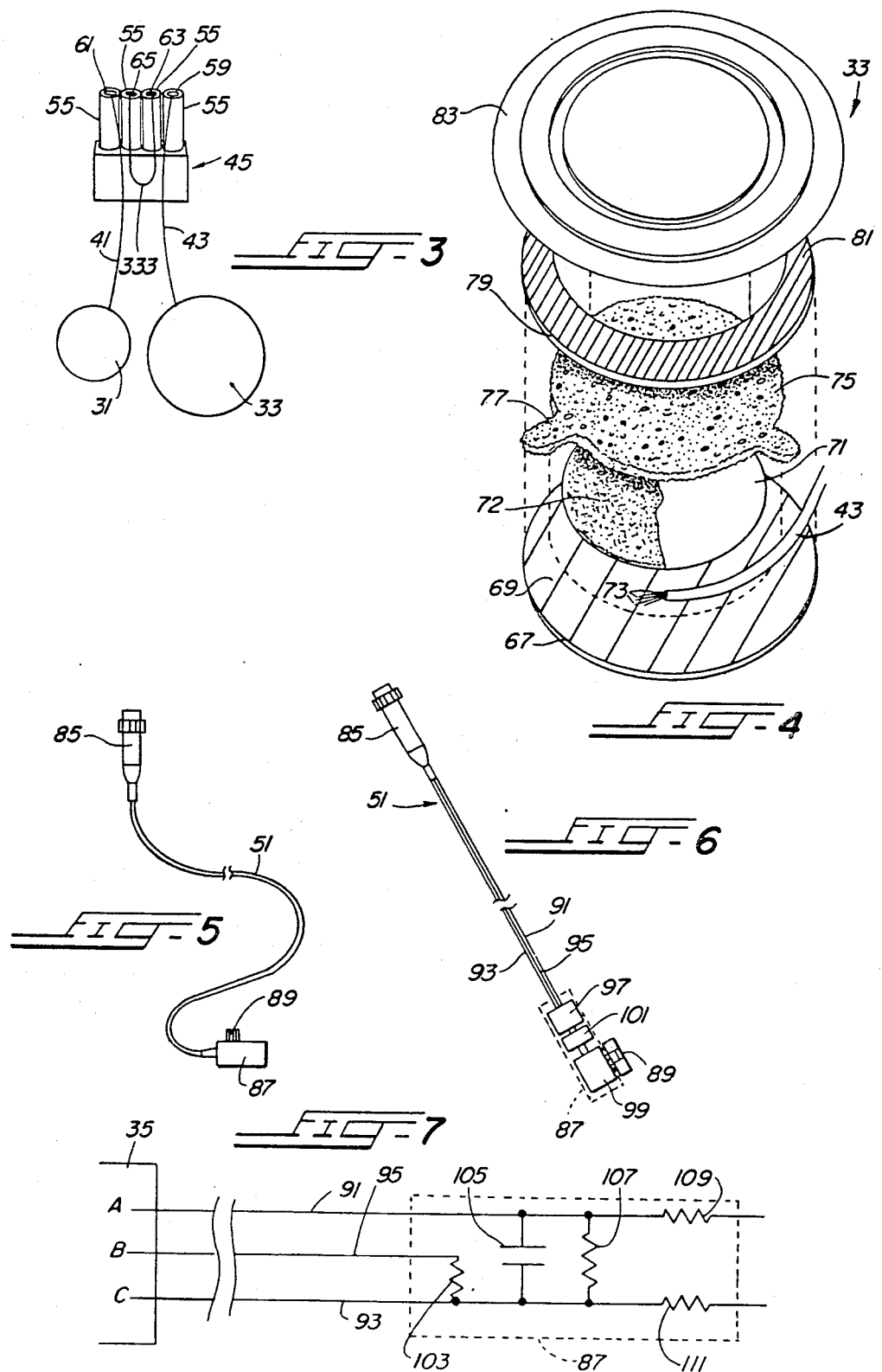

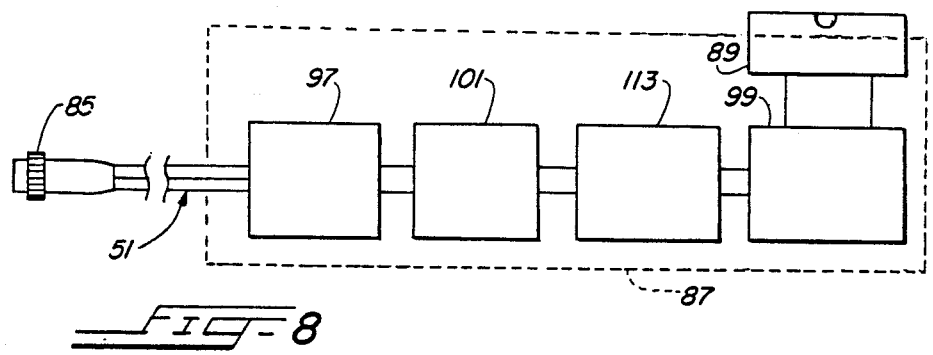
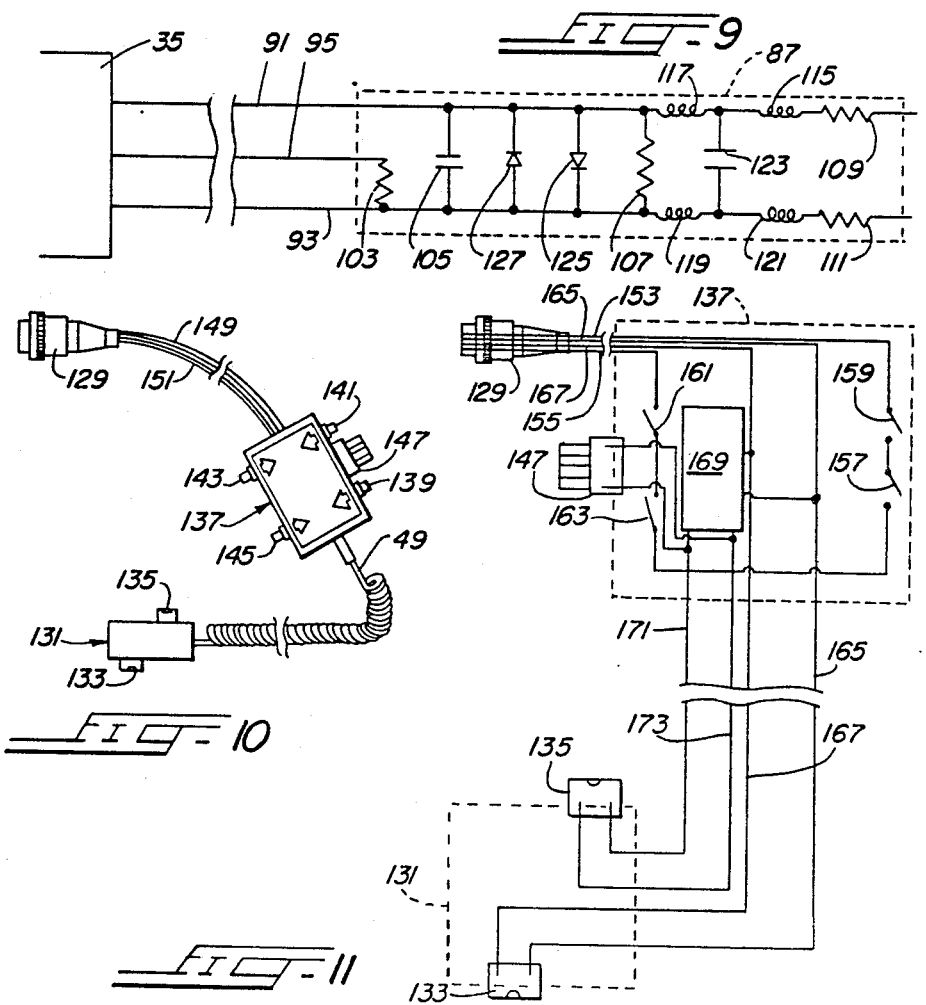

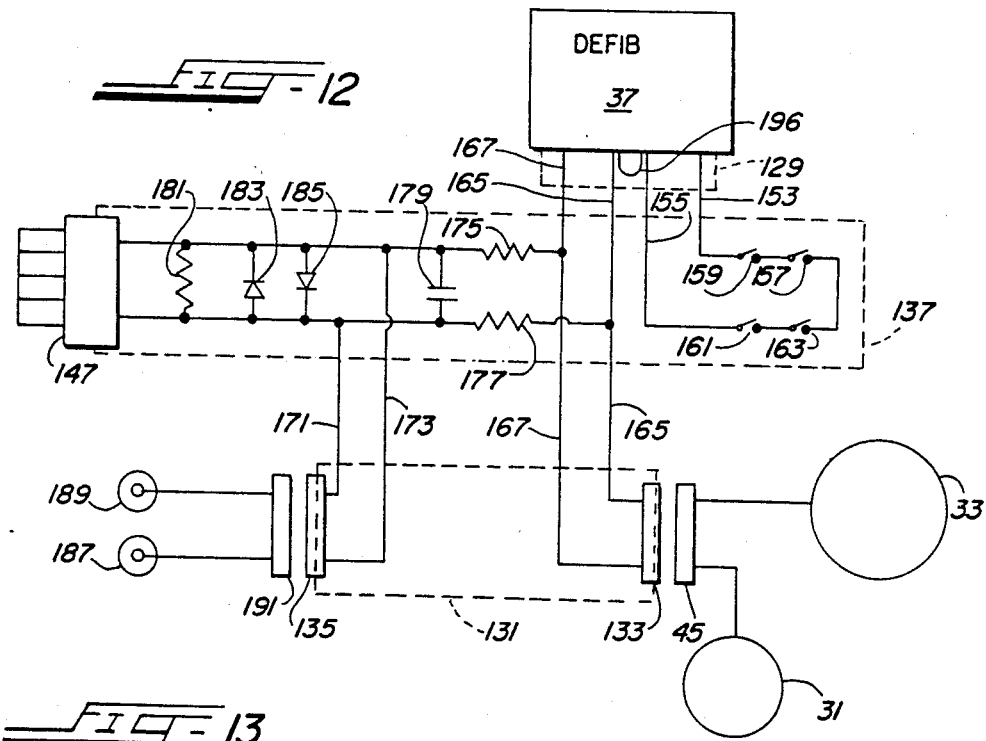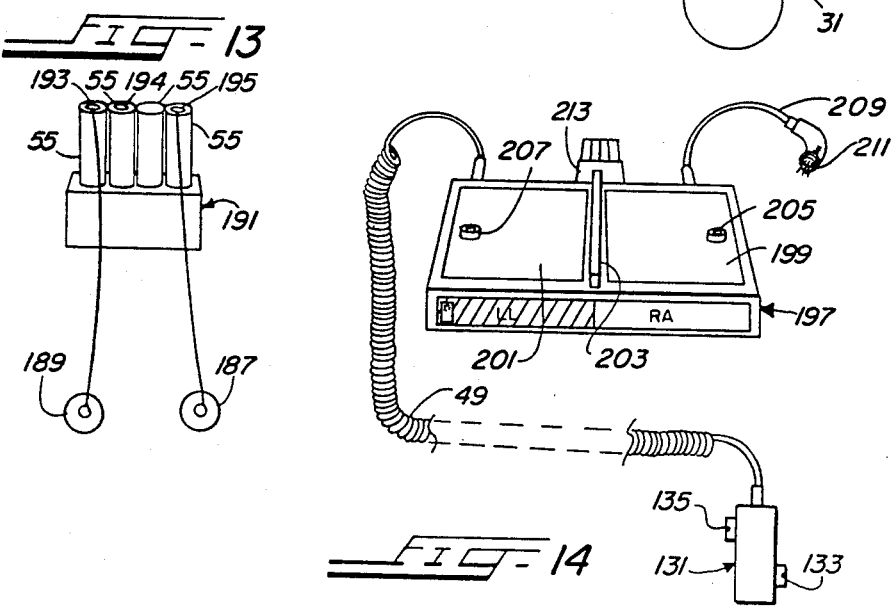

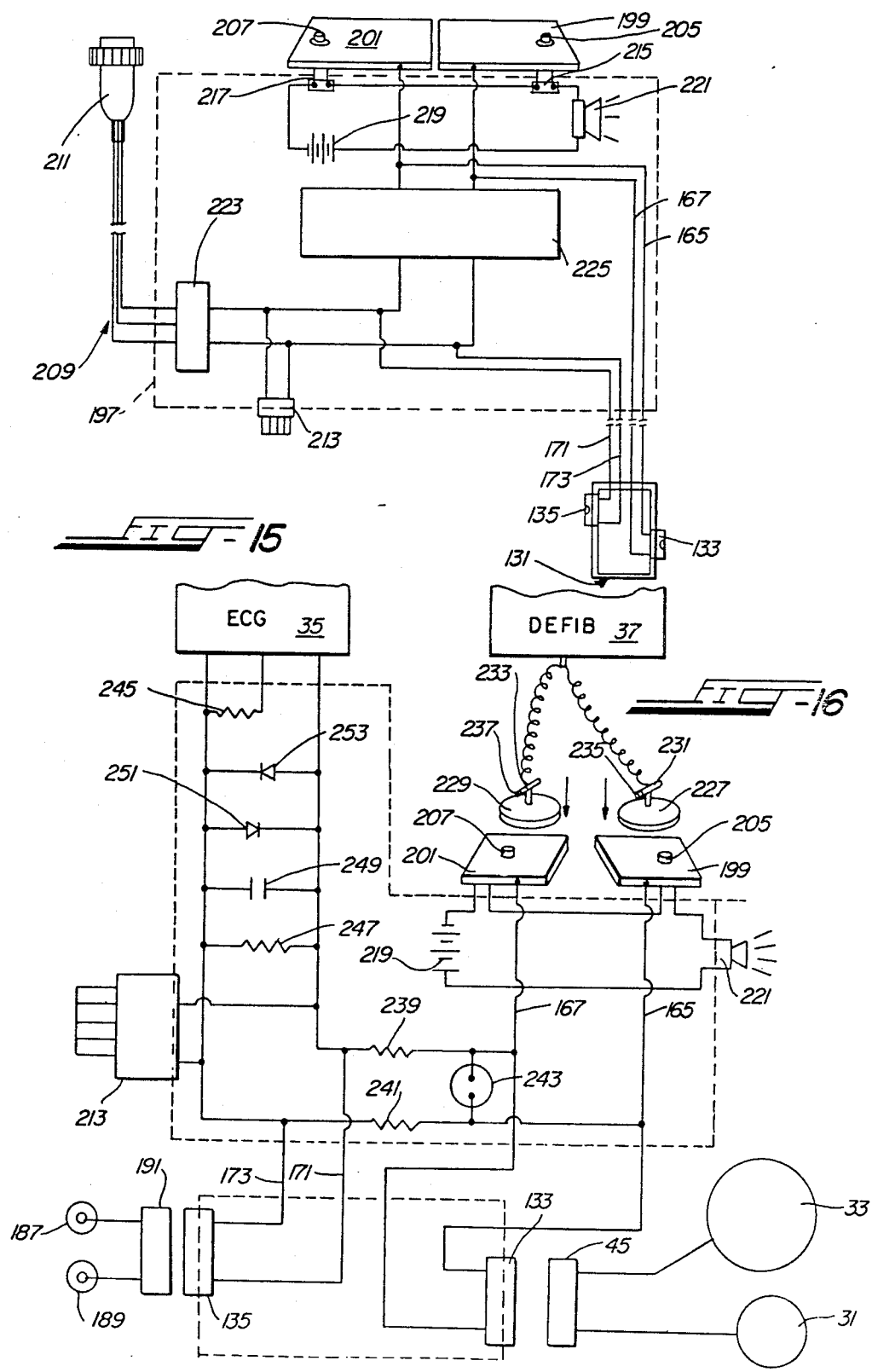

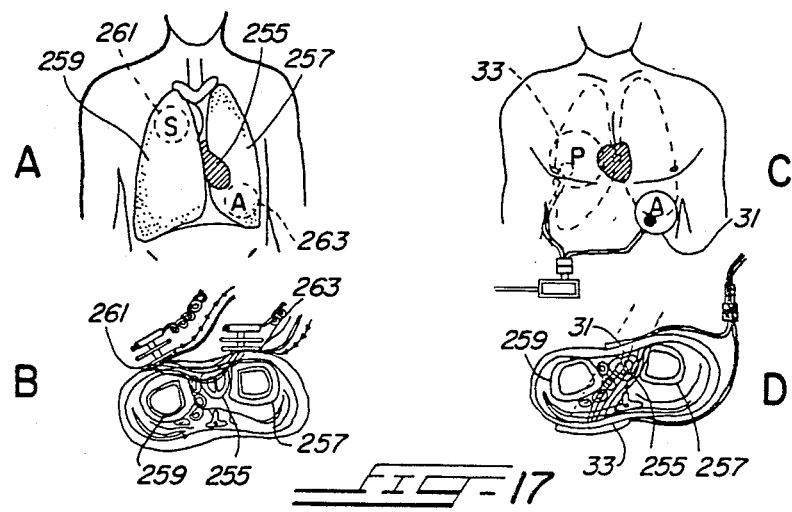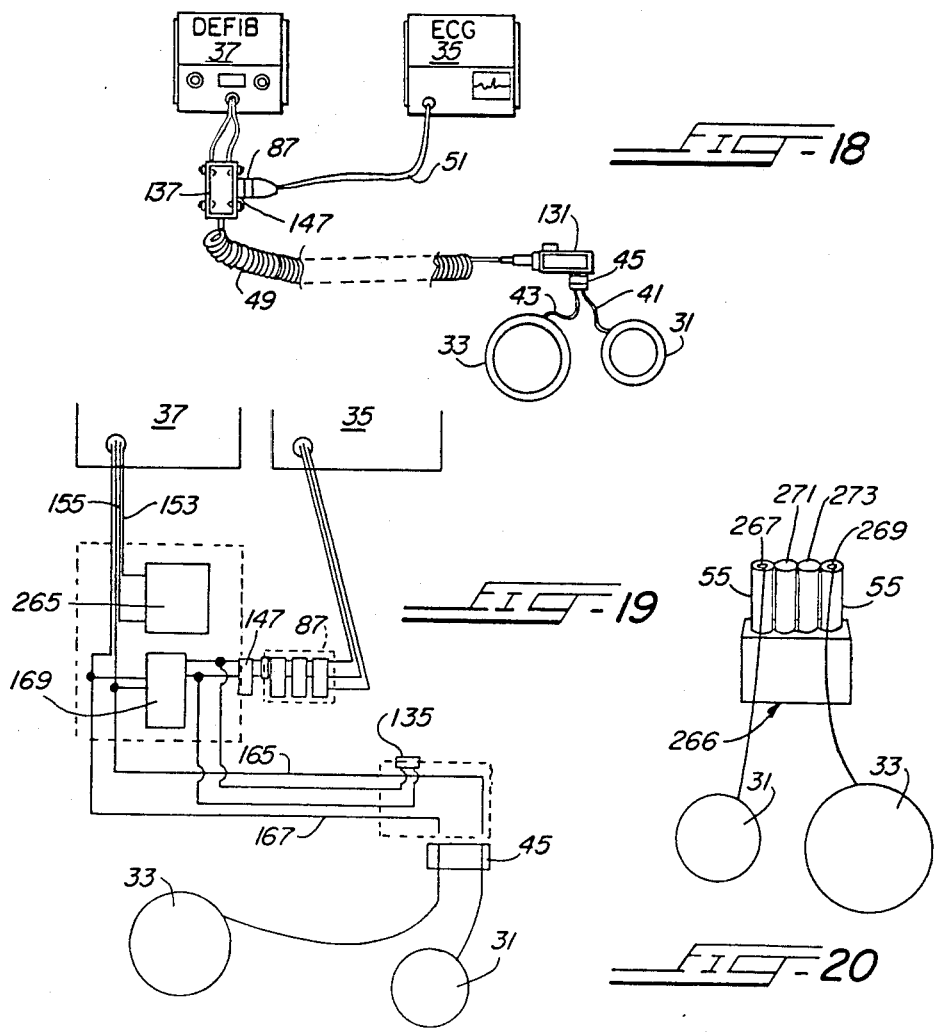

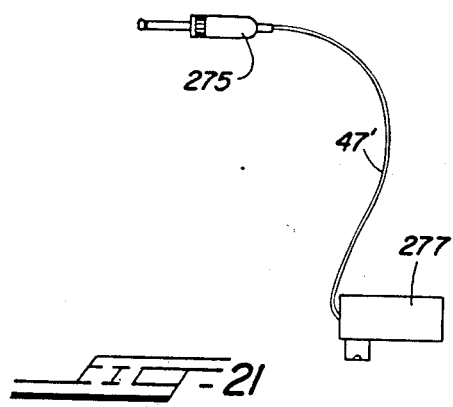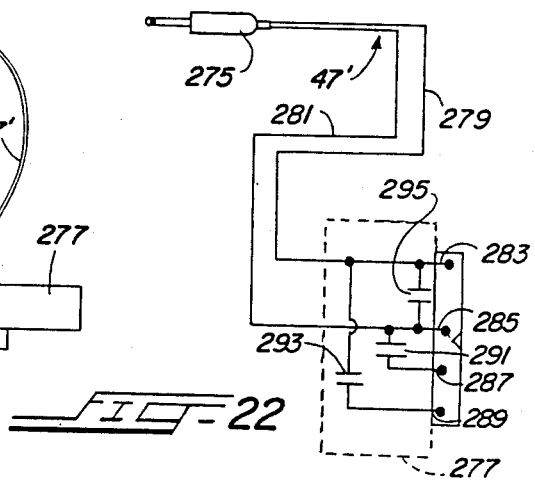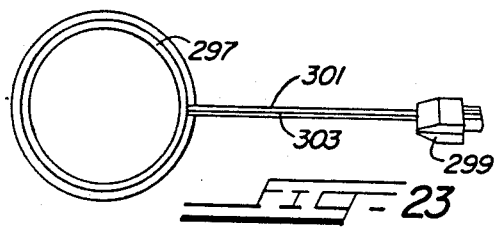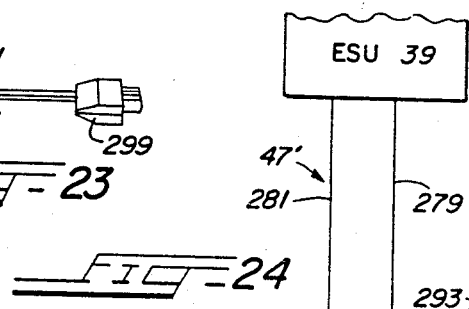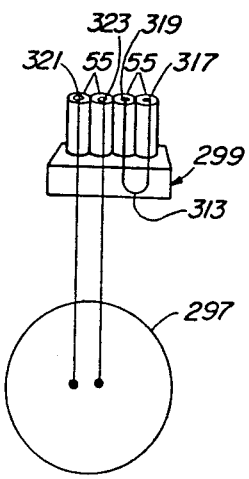

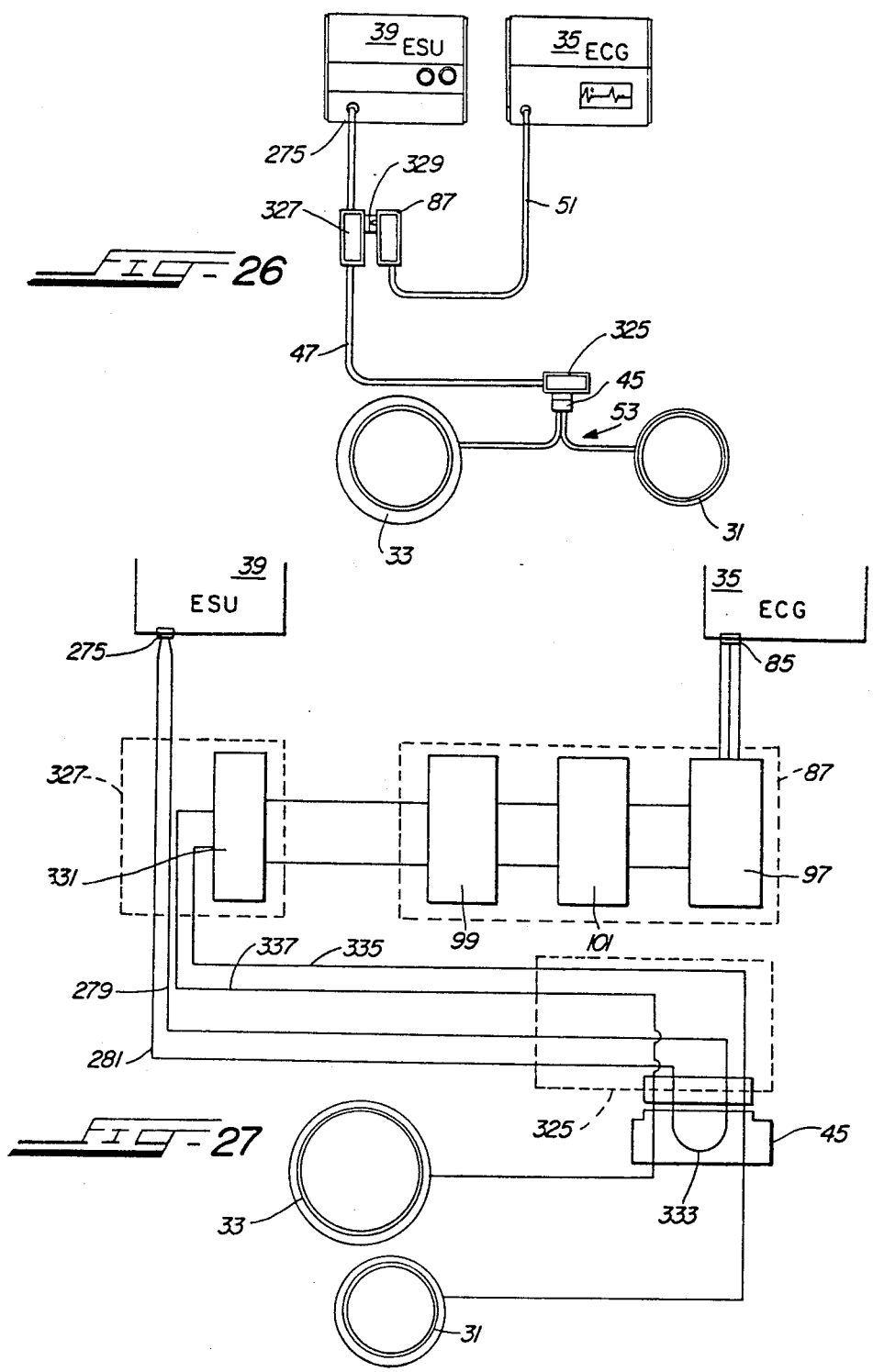

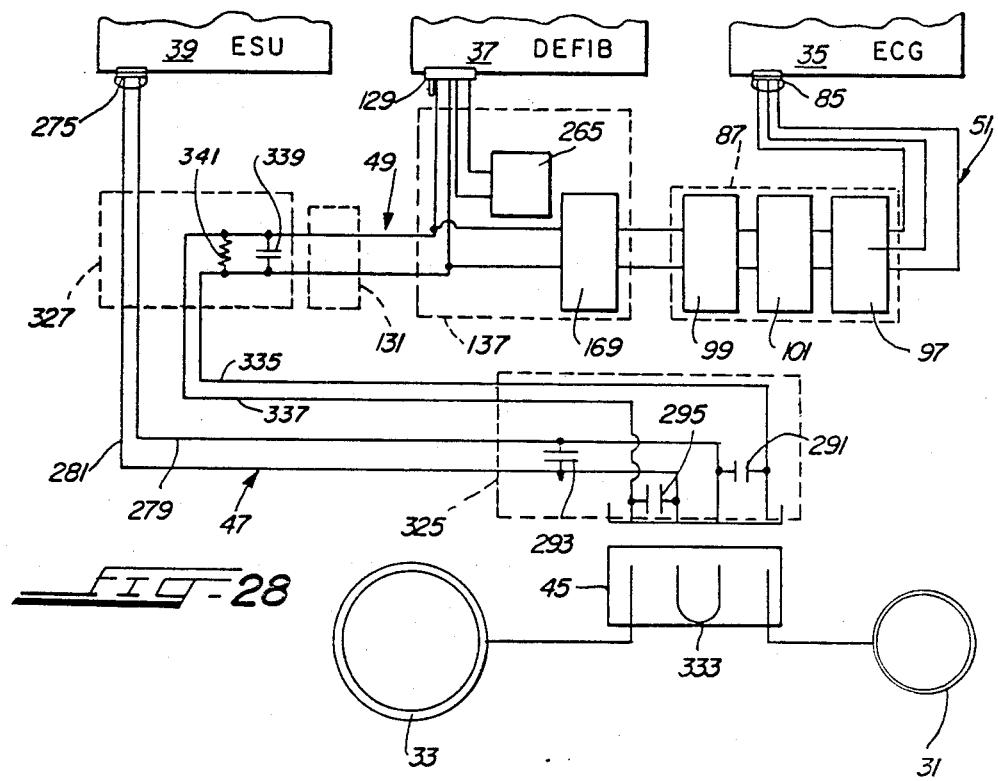

DISPOSABLE PHYSIOLOGICAL ELECTRODE SET

This is a continuation of U.S. patent application Ser. No. 946,168 (filed on 12/22/86 and now abandoned), which was a continuation of U.S. patent application Ser. No. 840,987 (filed on 3/14/86 and now abandoned), which was a continuation of U.S. patent application Ser. No. 712,919 (filed on 3/18/85 and now abandoned), which was a continuation of U.S. patent application Ser. No. 476,207 (filed on 3/17/83 and now abandoned), which was a division of application Ser. No. 176,270, filed Aug. 8, 1980, now U.S. Pat. No. 4,419,998 issued Dec. 13, 1983.

BACKGROUND OF THE INVENTION

1. Field of the Invention

This invention relates generally to physiological electrodes and their associated systems, and more specifically, this invention relates to physiological electrode systems by means of which a multiplicity of physiological functions may be achieved, either individually or in combination, through a single disposable electrode set.

2. Description of the Prior Art

Development of an understanding of electrical signals generated in the body and the utility of electrical signals supplied to the body has led to the necessity of transferring electrical energy to and from the body of a patient for medical purposes. This transfer of electrical energy to and from the body of a patient is achieved by means of electrodes contacting the skin of the patient. These electrodes may be generally classified as physiological electrodes.

Instruments or devices that are utilized in connection with physiological electrodes may be divided into three broad categories—monitoring devices, stimulating devices and therapeutic devices. Examples of monitoring devices include cardioscopes, electrocardiographs and electrocardiograms (for ease of reference the term "ECG" will be utilized to mean all or any of these devices) for monitoring operation of the heart and impedance pnuemographs for monitoring respiration. Therapeutic devices include electrosurgical units (ESU) and various radio frequency (RF) and other relatively high frequency applicators to reduce pain and promote healing. In the stimulating device category, there are defibrillators (used to shock a patient from fibrillation, an asynchronous cardiac ventricular or fluttering made of contractions) and other direct current (DC) and low frequency applicators. The line between a therapeutic device and a stimulating device is not always clear, but for purposes of this discussion a therapeutic device shall refer to an instrument involving high frequency signals (approximately 100 Hz. and higher), while a stimulating device is hereby defined as one employing DC or low frequency (approximately 60 Hz and lower) signals.

Most commonly, ECG electrodes are small (on the order of ½ inch) conducting plates from which an electrical connection to the patient's skin is achieved by means of a saline gel. Each electrode has its own individual electrical lead to the ECG and a total of from three to seven electrodes (even more in the case of some diagnostic testing) are utilized for cardiac monitoring. The electrodes are generally disposable so that they are discarded after a single use, while the leads are retained. New electrodes are usually connected to the leads by a snap-on connection.

There are a number of problems associated with ECG electrodes of this type. For one thing, the multiplicity of separate leads means that the leads are continuously getting twisted together, thus creating storing and handling problems. With the twisted leads, it is also a problem to assure that proper connections are effected, even with color coding or similar attempts to minimize erroneous connections. Also, movement of the leads creates electrical signals, possibly by a piezoelectric-type effect, which cause distortion of the ECG signal with what are commonly known as motion or cable artifacts. Further, voltage potentials between the electrodes can produce displacement of the baselines of the ECG signals or traces by an effect known as DC offset which can, in severe cases, preclude the obtaining of an ECG trace. Variations of the DC offset with time produces a drift of the ECG baseline that further complicates evaluation of the ECG signals. Still another problem associated with ECG electrodes is the existence of noise on the ECG trace occurring as a result of too high of an impedance between the electrode and the patient's body. The existence of too high an impedance is frequently compounded by the fact that the electrodes are too rigid to accurately conform to the portion of the body on which they are located, so that the area of contact between the electrode and the body is reduced, thus increasing the resistance or impedance (contact impedance) of the electrical circuit at that point. In most ECG electrode arrangements, the snap for connecting the lead to the electrode is right over the center of the electrode, so that any tension on the lead tends to lift the electrode from the body and hence increase the impedance. Fluctuations in the tension on the lead will also vary the contact impedance at the electrode-body interface by changing the pressure on the gel and thereby form another source of artifacts.

Conventional defibrillators utilize a pair of paddles to which handles are attached for an operator to press the paddles against the patient's body. A saline gel is placed on the paddles before they are applied to the patient to provide the desired interface between the paddles and the skin of the patient. As the paddles are pressed against the chest of the patient, a high voltage pulse of defibrillating energy is passed to the patient's body by actuation of discharge control buttons in the paddle handles.

One of the most disadvantageous features of the conventional defibrillator is that the operator is immediately adjacent the point of discharge. Thus, the risk that the operator will get shocked is not insignificant.

From the standpoint of efficacy, a major disadvantage of the conventional defibrillator paddles is that both paddles are applied to the chest of the patient. Testing has shown that for the best results in defibrillation it is desirable to have one of the defibrillating electrodes on the front of the body and the other on the back. Not only does this provide more current to the heart to increase the chances of a successful conversion (resuscitation by converting the heart from fibrillation to a life-sustaining rhythm), but it also reduces localized current densities, which test results suggest produces less myocardial damage. It is, of course, very difficult, if not almost impossible, in an emergency situation to prop a patient up so that one paddle can be pressed against the chest and the other against the back of the patient.

Yet another disadvantage of having both paddles on the chest of the patient is that a conducting path can be established over the skin of the patient from one paddle to the other, thus reducing the energy passed through the body tissue to the heart and also increasing the chances that a patient may be burned at the paddles. A further negative aspect of conventional paddles is that they are very difficult to apply to a patient that is draped for surgery or to whom a cardiopulminary resuscitation (CPR) device is attached. Still another problem with convention paddle defibrillators is that the paddle-to-skin impedance may be too high, thereby causing energy loss and increasing the risk of skin burns. A number of factors contribute to this undesirably high impedance, one of them being the rigidity of the paddles which prevents them from sufficiently conforming to the portion of the body to which they are applied. This problem may be overcome to some degree by pressure applied to the handles, but other factors such as insufficient area, less desirable contact metals and the use of low-quality gels still make the impedance problem one of concern. It may be noted that an insufficient paddle area also provides less desirable current density patterns.

Finally, conventional paddle defibrillators have the disadvantage that when a patient begins fibrillation the paddles must be gelled before being applied to the patient. The greater the time between the onset of fibrillation and the application of a defibrillating pulse, the greater the possibility that the patient will not be successfully converted.

Some of these problems with paddle defibrillators have been at least partially resolved by a disposable defibrillator electrode set known as the "BI-PAK" sold by Zenex Corporation. While this device deals with the basic problem of a front-to-back (anterior-posterior) electrode placement, the impedance characteristics may be improved upon. In addition, the "BI-PAK" does not provide for the connection of the electrodes to a separate ECG or to an ESU.

In order to return RF energy entering the body from an electrosurgical knife, an ESU return pad is normally placed under or attached to the patient, with a conducting lead extending back to the ESU return terminal. Various shapes and sizes of these return pads have been utilized, as well as a variety of conducting materials.

Since the RF currents introduced into the body during the electrosurgical process are relatively large, there is a continual problem of extracting this RF energy from the patient's body without heating the pad and burning the skin due to current concentrations at the ESU pad. Frequently patients are burned despite the efforts to preclude such a result. Such burns usually occur as a result of a non-uniform current density at various locations of the ESU return pad, particularly about the outer perimeter thereof, which is referred to as an improper dispersion of the RF current. Another problem of prior art ESU return pads that does not appear to be recognized is the existence of DC or low frequency shocking that occurs during electrosurgical operations. Some of this undersired shocking is probably due to leakage currents reaching the body through the ESU pad. However, it appears that some DC or low frequency currents are an inherent aspect of electrosurgical operations, due to rectification of the RF signals during tissue cutting. With a continuous DC or low frequency current path through the ESU return pad and the lead back to the ESU, it seems that there exists an ever-present danger of shocking the patient by undesired DC and low frequency signals during an electrosurgical operation.

Apart from the problems associated with the ECG, defibrillator and ESU electrodes individually, significant problems are encountered when more than one of these instruments is used at the same time. Thus, while the patient is being monitored by an ECG, fibrillation may commence and it is necessary to apply a defibrillating pulse of energy to save the patient. Similarly, during an electrosurgical operation, the condition of the patient's heart will frequently be monitored by an ECG. Further, it may also be necessary to defibrillate during the electrosurgical operation.

Pulses of defibrillation energy while ECG electrodes or an ESU return pad are connected to the patient may produce burns under the electrodes or pad, as well as damaging the ECG and ESU instruments. High voltage protection circuits have been utilized to prevent these occurrences. However, the recovery time for an ECG trace after application of a defibrillator signal may take anywhere from a few seconds to over a minute. Loss of the ECG trace at the time of defibrillation is particularly crucial, since it is imperative to know if the defibrillation shock was successful in terminating the fibrillation. Also, while the high voltage protection circuits protect the patient from burns and the ECG from damage, they also tend to prolong the recovery time for the ECG trace.

RF signals from the ESU create additional problems for the ECG, as these relatively high energy signals can create burns under the ECG electrodes, as well as significantly interfering with the ECG trace (especially by lower harmonic distortion). Filter circuits have been utilized to protect the ECG from such RF interference, but such filters frequently reduce the amplitude of the ECG trace so that it becomes difficult to analyze.

One of the primary problems occurring at the present time is that efforts have been directed to isolate the ECG, the ESU and the defibrillator from one another to prevent the problems referred to above. However, these attempts at isolation have precluded the instruments from having a common reference, so that an additional hazard is created by potential differences between the instruments themselves.

SUMMARY OF THE INVENTION

With the present invention, a single pair of electrode elements may be utilized to selectively convey electrical energy between the body of a patient and a monitoring device, a stimulating device and a therapeutic device. (While the definitions set forth above are useful for purposes of this discussion, it should be realized that the physiological electrode system described herein also has applicability to devices that cannot be strictly classified. For example, in impedance cardiography, signals in the "therapeutic" frequency range are used to chart physiological changes for purposes of monitoring.) Each of these instruments may be connected to the patient's body through the electrode elements by itself or in combination with one or more of the other instruments by means of an appropriate interrelating arrangement. Protective features are incorporated into the physiological electrode system to minimize or eliminate the risks of injury to a patient and damage to one of the instruments.

For purposes of illustration and ease of explanation, the remainder of the summary description will relate to an ECG (monitoring device), a defibrillator (stimulating device) and an ESU (therapeutic device). A single pair of electrode elements are attached to the body of a patient to provide for ECG monitoring and defibrillation of the patient and to provide a return path for RF energy inserted into the patient's body during electrosurgery.

Preferably, the electrode elements are part of a disposable electrode set that includes the electrode elements, a connecting plug and a pair of conducting lines (the term "conducting" being used herein in the sense of the capability of electrical current conduction, not the existence of such current conduction at any given time), each of the conducting lines extending from the plug to an associated one of the electrode elements. The plug is standardized for connection to the ECG, the ESU or the defibrillator, or any desired combination thereof. In a preferred embodiment, the connecting plug has four contacts with two of the contacts each having a first end of a respective one of the conducting lines connected thereto. The other two contacts are electrically connected or jumpered to provide a DC cord fault test circuit for the ESU, as described in more detail below. Also, capacitive coupling, such as one or more capacitors, may be connected from one or both of the conducting lines to the jumpered or short circuited contacts to provide a path for the return of RF signals to the ESU.

The electrode elements must be capable of meeting the varying requirements of monitoring electrodes, stimulating electrodes and therapeutic electrodes. Thus, for ECG monitoring, when the electrode elements are attached to the body the impedance between the electrode elements and the skin of the patient should be as small as possible to prevent undesired attenuation of the ECG signals. Since the most effective approach for minimizing noise on the ECG trace is to have a high input impedance at the ECG with a low impedance at the electrode element-to-body interface, minimizing the element-to-skin impedance also aids in the reduction of interference. Another important aspect of the ECG electrode is that the polarization of the electrode material by a high energy electrical signal, such as a defibrillator pulse, should rapidly dissipate in order to permit recovery of the ECG trace. This recovery time should be as short as possible to permit as nearly continuous monitoring of the heart as possible. Still further, DC offset potentials between the electrode elements should be minimal and should be as stable as possible.

With respect to handling of the ESU signals, at least one of the electrode elements should have a size and shape that yields a desirable current distribution to reduce heating and minimize the risks of the patient being burned by an undesired current concentration at a small area. Since such an area of concentration will normally occur at the periphery of the electrode, desired RF dispersion is primarily a factor of the perimeter of the electrode element. Use of both of the electrode elements for the RF return aids in dispersion of the RF currents and further reduces the risk of burns.

Finally, the electrode elements must have a size and shape, as well as a sufficiently low electrode element-to-skin impedance when attached to the patient, to maximize the transfer of a desired pattern of stimulating energy to the patient's body while minimizing the risk of skin burns. In view of the high energies involved in defibrillation, the electrode elements must be capable of conducting such high energy stimulating signals, as well as high energy ESU or other therapeutic signals, without loss of any of the desired characteristics of the electrode elements.

In order to be able to achieve all of these characteristics, the preferred embodiment disclosed herein utilizes circular electrode elements each having an electrically conductive plate sufficiently thin to permit the conductive plate to substantially conform to the area of the patient's body to which it is attached. This conductive plate may be formed entirely of a desired conductive metal, or it may utilize a layer of the desired conductive metal coated or plated over another conducting base metal or even a non-conducting or partially conducting supporting base. In any event, an outer surface of the conductive plate is formed of the desired conductive metal. An electrically conductive medium, such as a saline gel, is located between the outer surface of the desired conductive metal and the skin of the patient to improve electrical energy transfer between the patient and the conductive plate. A chloride of the desired conductive metal is located between the conductive metal and the skin of the patient, such as by forming a layer of the chloride directly on the metal or by locating the chloride in the conductive medium. An appropriate adhesive, such as an adhesive layer on a supporting plastic foam structure, is utilized to attach the electrode element to the patient.

While any suitable conductive metal and its chloride may be utilized, it has been found that tin and stannous chloride are particularly useful in meeting the variety of requirements established for these multi-function electrode elements. Accordingly, in a preferred embodiment disclosed herein, the conductive plate may be formed entirely of tin, such as a tin foil, or by a coating of tin over a conducting base plate such as brass, or by a layer of tin over a non-conducting substrate such as a plastic material. The stannous chloride may be directly applied to the tin surface, such as by spraying a thin layer thereon, or it may be located in the conductive medium. However structured, the novel use of a metal-metal chloride for defibrillation and ESU return is made particularly feasible by the discovery of the highly advantageous features of the tin-stannous chloride electrode element. Not only does the tin-stannous chloride electrode element exhibit highly advantageous features for the multi-function electrode, but it has also exhibited superior characteristics for single function usage, such as ECG monitoring. In addition to its extremely desirable operating characteristics, the tin-stannous chloride electrode element is highly resistant to disfiguring corrosion that easily occurs in the presence of a saline gel, and thus this structure provides a much longer shelf life for disposable electrodes.

While the electrode elements could be directly connected to the instruments, as indicated above the desired approach by applicant is to utilize a disposable electrode set with conducting lines running from the electrode elements to the connecting plug. This connecting plug could be made to directly engage the desired instrument, but the preferred approach disclosed herein is to utilize a separate cable having an appropriate connector to engage the plug at one end and being electrically joined to the desired instrument or instruments at the other end. These cables may then be relatively permanent, with only the electrode sets being replaced for each usage.

For the ECG cable, an ECG monitor connector at one end of the cable is utilized to attach the cable to the ECG device or instrument. An ECG electrode connector at the other end of the cable is adapted to engage the connecting plug of the disposable electrode set. A pair of conducting leads extend from the ECG monitor connector to the ECG electrode connector to connect the electrode elements directly to appropriate ECG inputs.

Since most ECG instruments require a minimum of three inputs, the connection of the electrode elements directly to two of the inputs will not provide a suitable trace. Accordingly, it is necessary to provide a body tissue impedance simulating circuit so that the ECG thinks that it is receiving three inputs from the body. This body tissue impedance simulating circuit may take any suitable form ranging from a single resistor to a multiple resistive-capacitive network. Although this body tissue impedance simulating circuit may be placed at any appropriate position in the cable, it has been found particularly desirable to locate it in the ECG electrode connector, with a third conducting lead running from the circuit to a third input of the ECG.

In order to prevent high frequency interference, such as from the RF signals used in electrosurgery, a low pass filter is located in the cable. Similarly, to protect the ECG from high energy signals, such as a defibrillator pulse, a high voltage protection circuit is utilized in the cable. Finally, in order to further minimize the risk of RF burns occurring at the ECG electrode elements, an RF choke filter network may be located in the cable. While all of these circuits may be located at any appropriate place in the cable, the low pass filter, the high voltage protection circuit, and the RF choke filter network are preferably located in the ECG electrode connector.

By placing all of the signal attenuation elements at the end of the cable away from the ECG instrument, an additional benefit is achieved. This additional benefit is a significant reduction, virtual elimination, of cable motion artifacts. Presumably, this very significant reduction of cable motion artifacts occurs as a result of the piezoelectrically induced signals being dissipated across the impedance in the ECG electrode connector, rather than across the impedance of the ECG itself.

Therefore, with the present invention, ECG monitoring may be achieved with a single cable that overcomes the "rats nest" problems of prior art multiple ECG leads. In addition, the ECG instrument is protected from high frequency interference and potentially damaging high energy signals. Further, the possibility of RF burns occurring at the electrode elements may be reduced. By using the ECG cable with the electrode elements of this invention, noise interference may be further reduced, DC offset potentials and drift may be minimized, and the recovery time for an ECG trace after application of a defibrillator pulse may be minimized, all while providing a stronger ECG trace signal.

With respect to the defibrillator cable, there are two variations. In one of these variations, the conventional defibrillator paddles are completely replaced. In the other, an adapter is provided for permitting use of the defibrillator paddles with the electrode elements of this invention.

By using the flat disposable electrode elements of this invention, a desired front-to-back placement of the defibrillating electrodes may be easily achieved. This permits the application of more current to the heart to greatly increase the chances of successful defibrillation. At the same time, the provision of smaller and more uniform current densities over the entire heart considerably reduces the risk of myocardial damage. In addition, by being able to have the electrode elements already in place before fibrillation occurs, the time elapsed between the onset of fibrillation and the application of a defibrillating pulse is minimized. This aspect of pre-application also permits defibrillation of patients draped for surgery or to whom CPR equipment is attached.

A particularly useful placement of the electrodes is to have the front electrode located at the apex or left leg position, while the back or posterior electrode is located at the right arm position. Not only does this electrode element positioning yield very desirable defibrillating results, but the apex positioning of the front electrode element puts this element in a generally non-hairy portion of the body and the positioning of the posterior electrode removes it from the uneven spinal area, thus minimizing electrode-to-skin impedance problems and difficulties in getting proper adherence of the electrode element to the skin. Further, the apex positioning of the front electrode keeps this electrode from interfering with cardiopulmonary resuscitation (CPR) efforts that may have to be taken with respect to the patient. This means that ECG monitoring of the heart may be continued without disruption, and that the electrode elements can remain in position for immediate defibrillation if the heart should begin to fibrillate.

In the first version of the defibrillator cable, a defibrillator instrument connector is utilized to replace the connection of the conventional paddles to the defibrillator. A pair of conducting leads in the defibrillator cable extends from the defibrillator instrument connector to a defibrillator electrode connector, through which the defibrillator outputs may be connected directly to the electrode elements. A discharge control module is located in the defibrillator cable, preferably adjacent the defibrillator instrument end of the cable. The discharge control module has four plunger actuated switches connected to the defibrillator through another pair of conducting leads. All four plunger actuators must be depressed in order for a pulse of defibrillating energy to be passed to the patient through the defibrillator cable. By locating the discharge control module in the defibrillator cable, defibrillating control is thus spaced from the patient to protect the operator from electrical shocks.

An ECG output connector is provided on the discharge control module. This ECG output connector is adapted to engage the ECG electrode connector on an ECG cable to permit an ECG instrument to be connected to the electrode elements through the defibrillator cable. The ECG output connector is connected to the conducting leads in the defibrillator cable through a high voltage protection circuit. An impedance matching circuit may be connected between the high voltage protection circuit and the ECG output connector in order to improve the ECG signal and minimize interference. This circuit is particularly important in situations where the ECG signal is not only being displayed on a local instrument but is also being transmitted to a central unit, such as a base hospital for a paramedic system.

While the most logical approach for use of the defibrillator cable is to utilize the multifunction electrode set described above, so that the electrode elements may be utilized for ECG monitoring and are already in place if defibrillation is required, electrode elements for just ECG monitoring may be made less expensively. Accordingly, an option has been provided by which a pair of ECG electrodes may be utilized to provide monitoring through the defibrillator cable. A separate receptacle for the ECG electrodes is located on the defibrillator electrode connector. In order to prevent the ECG electrodes (which could not handle defibrillator pulses or ESU return signals) from being accidentally connected to the other receptacle, the ECG electrode plug is structured so that it will only fit the ECG only receptacle. In passing it may be noted that these ECG electrodes could be used with the ECG cable, if only ECG monitoring is desired.

An additional pair of conducting leads extends from the ECG-only receptacle to the ECG output connector side of the high voltage protection circuit in the discharge control module. If an impedance matching circuit is utilized, the connection would be between the high voltage protection circuit and the impedance matching circuit.

With reference to the paddle adapter version of the defibrillator cable, an adapter unit is secured to the end of the defibrillator cable away from the defibrillator electrode connector. The adapter includes a pair of conducting plates upon which conventional defibrillator paddles may be located. An insulating divider between these plates prevents accidental shorting of the defibrillator paddles. The conducting plates are connected to the defibrillator electrode connector, which is the same as the defibrillator electrode connector utilized with the discharge control module version, by a pair of conducting leads. A button actuator for a switch extends up through each of the conducting plates, so that when the paddles are properly positioned on the plates the button actuators close switches in a battery powered DC circuit to actuate an audible alarm buzzer. Actuation of the buzzer indicates to the operator that a proper conducting circuit is completed to apply a defibrillator pulse to the patient by actuating the discharge controls on the conventional paddles. The buzzer also serves to warn any other attendants to move away from the vicinity of the patient.

An ECG cable may be permanently affixed to the adapter, with an appropriate body tissue impedance simulating circuit for this ECG circuit located in the adapter. An ECG monitor connector is on the other end of the ECG cable. Alternatively, a plug or connector for engaging an ECG electrode connector could be provided. A high voltage protection circuit is located between the body tissue impedance simulating circuit and the conducting leads extending to the defibrillator electrode connector. A supplemental ECG output connector is also located in the adapter and connected between the high voltage protection circuit and the body tissue impedance simulating circuit. The conducting leads from the ECG-only receptacle in the defibrillator electrode connector are also connected between the high voltage protection circuit and the body tissue impedance simulating circuit.

With either of the defibrillator cable variations, defibrillator discharge control is achieved at a distance removed from the patient for optimum safety of the operator. In addition, the electrode element structure of relatively large size, flexibility and a metal-metal chloride, specifically tin-stannous chloride, conducting plate results in reduced electrode element to skin impedance and a better current density distribution. Further, the fact that the electrodes are pre-applied saves valuable time in applying a defibrillating pulse to the patient if fibrillation should occur. Additionally, the use of disposable electrodes permits accurate control of the type of gel utilized, as gels not specifically manufactured for defibrillation use can affect defibrillating operation.

An ESU cable has a pair of conducting leads extending from an ESU instrument connector to an ESU electrode connector. These conducting leads extend to the jumpered or short circuited contacts in the plug of the disposable electrode set to form a DC cord fault test circuit. A source of DC potential, such as a battery, in the ESU passes a signal over the conducting leads to actuate the ESU for operation. Thus, the cord fault tester assures that the ESU electrode connector and the connecting plug of the disposable electrode set have been properly joined to provide a return path for the ESU RF energy before the ESU may be operated.

Capacitive coupling between the conducting leads and the contacts of the ESU electrode connector that engage the other two contacts of the connecting plug provides a path for RF signals from the electrode elements to the conducting leads. This capacitive coupling preferably takes the form of a first capacitor connected from one of the contacts to one of the conducting leads, a second capacitor connected from the other contact to the other conducting lead, and a third capacitor connected between the two conducting leads. This capacitive coupling essentially provides a high pass filter that prevents DC and low frequency currents from passing to or from the ESU instruments. Thus, by using high power capacitors, the ESU may be fully protected from high energy DC signals, such as defibrillator pulses. In addition, the capacitive coupling protects the patient from low frequency and DC currents that are potentially capable of causing fibrillation. These low frequency and DC currents may either be leakage currents from the ESU or currents resulting from rectification of the RF current during the electrosurgical operation.

Rather than utilizing the disposable electrode set with its two electrode elements, the ESU cable may be utilized just for ESU return. For this purpose, a single RF return pad constructed in the same fashion as the electrode elements described above may be utilized, although a less expensive return pad using a suitable conducting material, such as aluminum, instead of the metal-metal chloride structure that is particularly adapted for defibrillating and ECG usage. A conducting line extends from the pad or electrode element to a contact of a connecting plug, which has two other contacts jumpered or short circuited for the cord fault test circuit. Capacitive coupling is provided in the ESU electrode connector to capacitively connect the conducting line to the conducting leads in the ESU cable. Alternatively, or supplementally, this capacitive coupling may be achieved in the connecting plug by a capacitor connected between the conducting line and the jumpered contacts. While a single conducting line as described provides an operative system, in the preferred embodiment disclosed herein a second conducting line is utilized between the return pad and the connecting plug, so that the ESU cable has the form described in connection with the two electrode elements. However, the connecting plug and the ESU electrode connector are designed so that this connecting plug cannot be engaged with a connector through which defibrillator pulses or ECG signals are intended to pass, since the single ESU return pad could not function for defibrillation or ECG monitoring.

Returning to the ESU cable adapted to utilize the disposable electrode set having a pair of electrode elements, an ESU cable connector is provided in the ESU cable intermediate the ESU instrument connector and the ESU electrode connector. This ESU cable connector has a prong arrangement the same as the connecting plug, so that an ECG electrode connector or a defibrillator electrode connector may be engaged therewith. A second pair of conducting leads extend from this plug portion of the ESU cable connector to the two non-jumpered contacts in the ESU electrode connector. A low pass filter, preferably located in the ESU cable connector, is connected in this second pair of conducting leads to prevent the RF signals from passing to an ECG or defibrillator connected to the ESU cable connector. In order to provide for the use of all three types of instruments in connection with the single pair of electrodes, a defibrillator may be connected to the ESU cable connector, and an ECG may be connected to the discharge control module or adapter of the defibrillator cable.

With the interconnections provided by this invention, a common reference is established for all of the instruments connected to the electrode elements. This common reference minimizes the problems of dangerous leakage between the instruments and also provides the basis for minimizing interference at one instrument resulting from the output of another instrument. Therefore, this invention provides physiological electrode systems in which a single pair of disposable electrode elements may be simultaneously connected to a plurality of instruments for performing a variety of functions. Not only does the invention provide for a multiplicity of functions, but it produces improvements in each of those functions, whether achieved through the multifunction arrangement or whether connected for separate operation.

These and other objects, advantages and features of this invention will hereinafter appear, and for purposes of illustration, but not of limitation, exemplary embodiments of the subject invention are shown in the appended drawing.

BRIEF DESCRIPTION OF THE DRAWINGS

FIG. 1 is a schematic diagram of a preferred embodiment of the present invention showing three instruments simultaneously connected to provide multiple functions through a single pair of electrode elements.

FIG. 2 is a more detailed view of the electrode elements connected in a preferred embodiment of a disposable electrode set.

FIG. 3 is a schematic diagram of the pin arrangement of the connecting plug in the disposable electrode set of FIG. 2.

FIG. 4 is an enlarged exploded view of one of the electrode elements of FIG. 2.

FIG. 5 is a schematic diagram of a preferred embodiment of an ECG cable.

FIG. 6 is a schematic illustration of the ECG cable of FIG. 5 depicting in greater detail certain features thereof.

FIG. 7 is a schematic circuit diagram of the ECG cable of FIGS. 5 and 6.

FIG. 8 is a schematic diagram illustrating another embodiment of the ECG cable of FIG. 5.

FIG. 9 is a schematic circuit diagram of the ECG cable of FIG. 8.

FIG. 10 is a schematic diagram of a preferred embodiment of a defibrillator cable.

FIG. 11 is a more detailed schematic diagram of the defibrillator cable of FIG. 10.

FIG. 12 is a schematic circuit diagram of the defibrillator cable of FIGS. 10 and 11.

FIG. 13 is a schematic diagram of the pin arrangement in the connecting plug for the ECG electrodes illustrated in FIG. 12.

FIG. 14 is a schematic diagram of another embodiment of the defibrillator cable.

FIG. 15 is a more detailed schematic diagram of the defibrillator cable of FIG. 14.

FIG. 16 is a schematic circuit diagram of the defibrillator cable of FIGS. 14 and 15.

FIG. 17 is a four-part schematic diagram illustrating conventional and a new defibrillator electrode placement.

FIG. 18 is a schematic diagram of a single pair of electrode elements simultaneously connected to a defibrillator and an ECG.

FIG. 19 is a more detailed schematic diagram of the system of FIG. 18.

FIG. 20 is a schematic diagram of the pin placement in the connecting plug for the electrode set illustrated in FIGS. 18 and 19.

FIG. 21 is a schematic diagram of a preferred embodiment of an ESU cable.

FIG. 22 is a more detailed schematic diagram of the ESU cable of FIG. 21.

FIG. 23 is a schematic diagram of a preferred embodiment of a disposable ESU return pad set.

FIG. 24 is a schematic circuit diagram of the disposable ESU return pad set of FIG. 23 and the ESU cable of FIGS. 21 and 22.

FIG. 25 is a schematic diagram of the pin placement in the connecting plug for the ESU return pad set of FIGS. 22 and 23.

FIG. 26 is a schematic diagram of an ESU and an ECG simultaneously connected to a pair of electrode elements.

FIG. 27 is a more detailed schematic diagram of the system of FIG. 26.

FIG. 28 is a more detailed schematic diagram of the system of FIG. 1.

DETAILED DESCRIPTION OF THE PREFERRED EMBODIMENTS

A preferred embodiment of a physiological electrode system constructed in accordance with this invention is illustrated in FIG. 1. A single pair of electrode elements 31 and 33 are simultaneously connected to an ECG instrument or device 35, a defibrillator instrument or device 37, and an ESU instrument or device 39. Of course, these instruments could be any type of monitoring, stimulating and therapeutic devices, as defined above.

Electrode elements 31 and 33 could be any type of suitable electrode placed on the body of a patient, but in this preferred embodiment these electrode elements are single-use elements arranged in a disposable electrode set. In this preferred embodiment, electrode element 31 is approximately 8 centimeters in diameter and electrode element 33 is approximately 12 centimeters in diameter, although any appropriately sized electrodes may be utilized. An interrelating arrangement includes conducting lines 41 and 43, a connecting plug 45, an ESU cable 47, a defibrillator cable 49 and an ECG cable 51. Details of this interrelating arrangement and of the protective circuits and approaches that permit the simultaneous connection of a plurality of instruments to a single pair of electrode elements to achieve a multiplicity of functions are set forth hereinafter.

A disposable electrode set 53 is shown in more detail in FIG. 2. This disposable electrode set includes the electrode elements 31 and 33, conducting lines 41 and 43 and the connecting plug 45. Connecting plug 45 is a standardized plug that may be connected to the ESU cable 47, or the defibrillator cable 49, or the ECG cable 51. Although the connecting plug 45 may be constructed with two or three contacts for certain applications, in order to achieve the desired multi-function capabilities, plug 45 should have four contacts.

While plug 45 could be any appropriate type of connecting plug, in this preferred embodiment connecting plug 45 has the structure illustrated with projecting insulating sheathes 55, in which are located conducting prongs or contacts 57. Conducting prongs or pins 57 may either be solid, male prongs, or hollow, female prongs. These prongs may be arranged in appropriate patterns to preclude undesired engagements of the connector plug with other connectors. For example, as illustrated in FIG. 3, the outer two prongs 59 and 61 are female, while the inner two prongs 63 and 65 are male. In order for this plug to engage a connector, the connector must have male prongs at the outer contacts and female prongs at the inner contacts. Electrode set 53 is for use with all types of functions, so the ECG, the defibrillator or the ESU, may be connected to electrode elements 31 and 33 separately or in various combinations, so long as the connector on the cable utilized has the appropriate pin arrangement.

Referring back to FIG. 2, it may be seen that connecting plug 45 has an easily assembled structure consisting of two casing components 66 and 67. Although any appropriate structure could be utilized, of course, this structure provides a complete and yet easily assembled connecting plug.

A preferred assembly or structure of the electrode elements 31 and 33 is depicted in FIG. 4. Although various shapes of electrodes might be utilized, it has been found that the circular or round shape disclosed herein has certain advantages, as discussed in more detail hereinafter. Also, it may be noted that the description of the circular electrode element shown in FIG. 4, which has been identified as electrode element 33 for purposes of illustration, relates to the preferred structure of all of the electrode elements discussed in this application.

A circular foam base 67 having a layer of adhering material (adhesive) 69 on one side thereof provides the bottom or basic layer of the electrode element. While base 67 is preferably formed from a plastic foam, it may be made of any suitable insulating material that is relatively rigid but with some degree of flexibility. Labeling may be affixed to the side of base 67 away from the adhesive layer 69, although this labeling should not be sized or located in a way that will not significantly restrict the flexibility of the electrode element.

An electrically conductive plate 71 is then secured to the adhesive layer 69 of base 67. Conductive plate 71 preferably has a circular shape with a desired electrically conductive metal forming at least one surface thereof. A chloride of the conductive metal is located to be between the conductive metal and the skin of the patient, such as by spraying a layer 72 thereof on the conductive metal surface.

Although it is possible that other metal-metal chloride combinations could be successfully utilized (silver-silver chloride has been utilized for ECG electrodes), an important aspect of the present invention is the discovery that a tin-stannous chloride combination provides unexpected highly significant advantages over other types of materials. (It is possible that alloys formed primarily of tin would also provide some or all of the desired characteristics when used with stannous chloride.) Thus, measurements have revealed that the tin-stannous chloride electrode element can be utilized to produce a very low impedance between the electrode element and the skin of the patient. This result is especially significant in the case of ECG monitoring and defibrillation. In addition, the tin-stannous chloride electrode element conducts the high energy currents produced by defibrillation without apparent deterioration, while at the same time recovering very rapidly from the polarization caused by these high energy levels. In fact, the recovery of an ECG trace after the application of a defibrillating pulse is almost instantaneous, showing a significant improvement over prior art ECG recovery times. Measurements to date have indicated that the DC offset produced by utilizing tin-stannous chloride electrode elements is well within the accepted range and comparable or superior to existing devices. Very significantly, however, these measurements also show that the DC offset potential resulting from the utilization of tin-stannous chloride electrode elements was very stable, so that only a very small amount of drift of the ECG trace occurred.

The structure of electrically conductive plate 71 can take any of a variety of acceptable forms. For example, plate 71 could be formed completely of tin, such as a tin foil, or it could be a tin coating over a substrate. This substrate could be another conducting metal, such as brass, or it could be a non-conducting material, such as a plastic. In the preferred embodiment disclosed herein, a tin foil has been utilized.

In order to achieve electrical conduction between the conductive plate 71 and the conducting line 43, an electrical connection must be made between the conductive plate 71 and conductors 73 of line 43, from which the insulation has been stripped. Any suitable approach could be utilized, but in this preferred embodiment it has been found that the end of line 43 and the conductors 73 may be secured to the adhesive layer 69 before the tin plate 71 is adhered, so that when plate 71 is secured to the adhesive layer 69 a good electrical connection is established and maintained between the conductors 73 and the tin plate 71.

A porous foam disc 75 is then placed over the tin conductive plate 71. The porous foam disc 75 has been provided with lugs or ears 77 extending outwardly from the perimeter thereof to aid in securing disc 75 in the structure. The porous foam of disc 75 is adapted to receive and maintain an electrically conductive medium, such as a saline gel, to provide a good conductive path between the tin plate 71 and the skin of the patient. Any suitable type of conductive medium or gel may be utilized that meets the requirements for the various functions to be performed through the electrode elements. Particular attention, however, must be directed to the selection of a conductive medium or gel that provides the desired results during application of the high energy defibrillating pulses.

It has been noted that the stannous chloride may be associated with the tin plate 71 by spraying a layer 72 of the stannous chloride on the plate. This layer need not cover the whole surface of the plate 71, but could be in a smaller selected area, or in a number of selected areas. However, another possibility is to locate the stannous chloride right in the conductive medium, so that it is not necessary to actually affix the stannous chloride to the conductive plate 71.

A holding ring 79 is then positioned over the porous foam that contains or will contain the conductive medium. Ring 79 may be formed of any suitable material, but for ease of manufacture it is formed of the same foam material as base 67, in this preferred embodiment. Ring 79 is secured to the adhesive layer 69 on base 67 over the lugs or ears 77 to fix the foam disc 75 in place. In passing, it should be noted that other methods of securing the foam disc 75 in place could be utilized and that the extending lugs 77 are merely exemplary of a fastening approach utilized in this preferred embodiment. It should also be noted that ring 79 will normally be somewhat thicker than the base 67, as it provides a "pool" for the gel absorbed in the porous foam of disc 75. An adhesive layer 81 is formed on the top of ring 79.

Finally, a sealing cover 83 is secured to the adhesive layer 81 of the ring 79. The purpose of cover 83 is to provide a substantially air-tight or hermetic seal to prevent the gel in the disc 75 from drying out. This cover may be formed of any suitable material, but a thin, rigid, transparent plastic is utilized in the preferred embodiment disclosed herein. During operation, the cover 83 is removed from the electrode element and the electrode element is then attached to the patient by means of the adhesive layer 81 on ring 79.

Among the advantages of the circular electrode element is the uniform flexibility that is provided, so that the electrode element and the conductive plate 71 may accurately conform to the shape of the portion of the body on which the electrode element is placed. By being able to accurately conform the electrode and the conducting plate to the shape of the body, the largest possible conducting area is maintained, which reduces the contact impedance between the electrode element and the skin of the patient. This low impedance is especially important for ECG monitoring and defibrillation. With respect to the ESU, the circular nature of the electrode element and the conductive plate 71 provides the most uniform possible current distribution for RF dispersion. The flexibility of the electrode to conform to the shape of the body portion to which it is attached also contributes to a uniform contact area to prevent current concentrations that could result in RF burns.

A schematic illustration of a preferred embodiment of the ECG cable 51 appears in FIG. 5. Cable 51 is a shielded cable having an ECG monitor connector 85 at one end thereof. This ECG monitor connector 85 is adapted to engage the input jack of a standard ECG instrument. The ECG input jack is constructed to receive three or more ECG inputs.

At the other end of ECG cable 51 there is an ECG electrode connector 87. This ECG electrode connector 87 may be any appropriate arrangement to engage the connecting plug 45, but preferably this ECG electrode connector 87 has a standard configuration that may also be used with the ESU and defibrillating cables 47 and 49. The preferred form shown herein is that of a rectangular box with enough internal space to receive the various circuits included in the different electrode connectors of the various cables. A receptacle 89 extends outwardly from the box of connector 87 to engage the plug 45.

FIG. 6 is a partial circuit diagram of the cable of FIG. 5 illustrating the cable in more detail. As may be seen, there are three conducting leads 91, 93 and 95 extending from the ECG monitor connector 85 to the ECG electrode connector 87. A body tissue impedance simulating circuit 97 is included in the connector 87, together with a high voltage protection circuit 99. Body tissue impedance simulating circuit 97 provides for the use of an ECG, which normally requires three or more inputs, with only the two electrode elements 31 and 33. High voltage protection circuit 99 is included to protect the ECG from high energy signals, such as defibrillator pulses. In addition, a low pass filter 101 is located in connector 87 with the body tissue impedance simulating circuit 97 and the high voltage protection circuit 99. Low pass filter 101 serves to minimize the interference from RF signals, such as those produced by an ESU, and other relatively high frequency signals that can distort the ECG trace and render analysis difficult.

In the more detailed circuit diagram of FIG. 7, it may be seen that the conducting leads 91 and 93 are connected directly from two inputs of the ECG 35 (these inputs having been designated A and C) to contacts of the receptacle 89 (FIG. 6) that will result in inputs A and C being connected to the electrode elements 31 and 33. Body tissue impedance simulating circuit 97, to which the third ECG input B is connected by a conducting lead 95, is represented as a single resistance 103. While a single resistor may be appropriate in some conditions, the body tissue impedance simulating circuit 97 may also involve multiple resistor networks or resistive-capacitive networks. The exact structure of the body tissue impedance simulating circuit 97 is such that it will produce at the ECG the appearance of three inputs rather than the two inputs that are actually received. Either of the inputs B or C may be the reference or ground lead for the ECG.

Low pass filter 101 is illustratively indicated as a capacitor 105 and a resistor 107 connected in parallel between lines 91 and 93. Of course, this circuit is representative only and any appropriate low pass filter circuit may be utilized.

High voltage protection circuit 99 is illustratively depicted as a pair of series resistances 109 and 111 connected in lines 91 and 93, respectively. Again, the high voltage resistance circuit 99 may take any appropriate form, although a pair of series resistors 109 and 111 will normally suffice to provide the desired protection.

To further ensure against the establishment of any conductive path for RF signals, such as when only smaller ECG electrodes are going to be connected to the cable 51 which thus increases the risk of RF burns at these electrodes, an RF choke filter 113 may be added to connector 87, as illustrated in FIG. 8. With reference to FIG. 9, an illustrative choke filter 113 includes choke coils 115, 117, 119 and 121 and a capacitor 123. Of course, this particular circuit is only representative and any appropriate RF choke filter arrangement could be employed.

Another variation of the circuitry that may be employed is the addition of oppositely poled diodes 125 and 127 connected between leads 91 and 93 in the low pass filter 101. Diodes 125 and 127 aid in the filtering of relatively high frequencies that could distort or interfere with the ECG trace, such as "shot" noise. While the circuits 97, 99 and 101 could be located at any place in cable 51, the placement of these circuits in connector 87 not only simplifies manufacture, but also aids in greatly reducing motion artifacts by having all of the signal attenuation located at the electrode end of the cable. Artifacts produced by movement of the cables while ECG signals are being obtained from a patient are dissipated to a great extent across the impedances at this end of the cable, with the result that very little effect therefrom is experienced at the ECG instrument itself. Diodes 125 and 127 also aid in protecting the ECG from defibrillating pulses by substantially short circuiting leads 91 and 93 through the high voltage protection circuit 99.

Defibrillator cable 49 is schematically illustrated in FIG. 10. A defibrillator instrument connector 129 is located at one end of cable 49, while a defibrillator electrode connector 131 is positioned at the other end thereof. Defibrillator electrode connector 131 has a receptacle 133 to engage connecting plug 45. Connector 131 is also provided with a second receptacle 135 to engage a connecting plug for a pair of ECG electrodes, in the event that it is desired to use cable 49 only for ECG monitoring, without a defibrillating capability until a connecting plug 45 is engaged with receptacle 133 and electrode elements 31 and 33 are attached to the patient.

A defibrillator discharge control module 137 is located in cable 49. Discharge control module 137 has four plunger actuators 139, 141, 143 and 145, all of which must be depressed in order to pass a defibrillating pulse through cable 49 to electrode elements 31 and 33 on the patient. An ECG output terminal 147 has a plug portion corresponding to connecting plug 45 to engage an ECG electrode connector receptacle 89 to provide for ECG monitoring through cable 49. Separate cable portions 149 and 151 extend from discharge control module 137 to the instrument connector 129. Cable portion 149 contains the conducting leads to carry the defibrillating current, while cable portion 151 contains conducting leads for a discharge control circuit.

From the partial circuit diagram on FIG. 11, more details of the cable 49 may be observed. Thus, it may be seen that cable portion 151 contains the conducting leads 153 and 155, which are series connected through switches 157, 159, 161 and 163, corresponding, respectively, to plunger actuators 139, 141, 143 and 145. Also, it may be seen that cable portion 149 contains conducting leads 165 and 167 which continue through the discharge control module 137, to thus extend from the defibrillator instrument connector 129 to receptacle 133 in the defibrillator electrode connector 131. A high voltage protection circuit 169 is connected between the ECG output terminal 147 and the conducting leads 165 and 167. Another pair of electrically conducting leads 171 and 173 connects the ECG-only receptacle 135 in connector 131 to the ECG output terminal 147. Conducting leads 171 and 173 are connected to terminal 147 on the plug side of the high voltage protection circuit 169, so that this high voltage protection circuit also protects an instrument connected to leads 171 and 173 from the defibrillating energy on leads 165 and 167.

In the more detailed circuit diagram of FIG. 12, further details of the defibrillation cable 49 may be observed. Thus, it may be seen that the high voltage protection circuit 169 includes a pair of large series resistors 175 and 177 and a capacitor 179 connected across the lines. It should be observed once again that this is merely an illustrative circuit and that any appropriate high voltage circuit arrangement could be utilized. It may also be seen that an impedance matching circuit including a resistor 181 and oppositely poled diodes 183 and 185 is connected across the ECG output terminal 147. While this impedance matching circuit may be utilized in connection with any ECG, it is particularly adapted for use in remote or emergency situations in which the ECG trace is transmitted to a central unit or hospital by telemetry. Conducting leads 171 and 173 from the ECG-only receptacle 135 are connected between this impedance matching circuit and the high voltage protection circuit 169.

A disposable set of ECG electrodes 187 and 189 and an ECG electrode connecting plug 191 are schematically illustrated in FIG. 12. The plug 191 is adapted to engage the ECG-only receptacle 135 of the defibrillator electrode connector 131. Plug 191 and receptacle 135 are specially designed so that the connecting plug 191 could not engage, for example, the receptacle 133, since the ECG electrodes 187 and 189 could not handle the defibrillating energy from lines 165 and 167. To prevent the ECG electrodes 187 and 189 from being connected to lines 165 and 167, FIG. 13 shows that although the ECG connecting plug 191 has female prongs 193 and 195 in the outer insulating sheathes 55 to permit connection to plug 45, a female prong 194 has been located in one of the inner sheathes 55. Thus, plug 191 could not be engaged with receptacle 133, which would also have a female prong in the inner contact or sheathe position, thus preventing any possibility of defibrillation energies being conveyed to ECG electrodes 187 and 189.

ECG electrodes 187 and 189 could be conventional ECG electrodes, specially designed ECG electrodes or smaller versions of the electrode element illustrated in FIG. 4. For example, the ECG electrodes could be constructed in the same fashion as the element of FIG. 4 but having a diameter in the vicinity of 4 centimeters. Such a pair of electrode elements has proved to be very satisfactory for ECG operation. In addition to the other benefits discussed above, such an ECG electrode has the further advantage that the lead 43 comes from out the side of the electrode element. Since conventional snap-type ECG electrodes have the snap directly over the center of the electrode, tension on the lead to the snap varies the gel pressure and produces electrode motion artifact on the ECG trace. With the lead coming out the side of the electrode element, most of these artifacts can be eliminated. This reduction of artifacts emanating from the electrode elements is also true of electrode elements 31 and 33.

A final comment with respect to the structure of defibrillator cable 49 is that a shorting jumper 196 may be located in the defibrillator instrument connector 129 to adjust for the application of adult defibrillating energies or child or internal defibrillating energies.

A variation of defibrillator cable 49 is illustrated in the schematic diagram of FIG. 14, in which a paddle adapter 197 is located at one end of cable 49, with the defibrillator electrode connector 131 still positioned at the other end of cable 49. Rather than describe each of the elements of this variation of cable 49, the same or similar parts have been identified by the same numerals for ease of reference.

Paddle adapter 197 has a pair of conducting plates 199 and 201 adapted to receive conventional defibrillator paddles and form a continuous electrically conducting path. Conducting plates 199 and 201 are separated by an insulating divider 203 to prevent accidental shorting of the defibrillator paddles. Button switch actuators 205 and 207 extend upwardly from conducting plates 199 and 201, respectively. When both of the button actuators 205 and 207 are depressed by defibrillator paddles, an audible alarm is produced to indicate to the operator that an appropriate defibrillating connection has been achieved and to warn other attendants to move away from the area surrounding the patient.

An ECG cable 209 is shown as permanently affixed to the paddle adapter 197 in this preferred embodiment (although alternatively a plug or connector could be provided for external connection through an ECG cable 51), and an ECG monitor connector 211 is located at the end of this cable 209. An ECG output terminal 213 is also provided on the paddle adapter 197 for connection to another ECG instrument, or for connection to a telemetry unit for transmittal of the ECG signals to a central unit or hospital.

Further details of the defibrillator cable 49 with the paddle adapter 197 are illustrated in FIG. 15. In this Figure, it may be seen that button actuators 205 and 207 close corresponding switches 215 and 217, respectively, when the actuators are depressed. This completes the circuit to a suitable energy source, such as a nine volt DC battery 219, to actuate a buzzer 221. ECG cable 209 has three conducting leads that extend from the ECG monitor connector 211 to a body tissue impedance simulating circuit 223 located in the paddle adapter 197. Body tissue impedance simulating circuit 223 is connected to the main conducting leads 165 and 167 through a high voltage protection circuit 225. ECG output terminal 213 is connected between the body tissue impedance simulating circuit 223 and the high voltage protection circuit 225, since this connector would engage the ECG electrode connector of an ECG cable in which a body tissue impedance simulating circuit would already be present. Conducting leads 171 and 173 from the ECG only receptacle 135 in connector 131 are also connected between the body tissue impedance simulating circuit 223 and the high voltage protection circuit 225.

The more detailed circuit diagram of FIG. 16 provides further explanation of the defibrillating cable 49. Thus, conventional defibrillator paddles 227 and 229 are schematically illustrated for engagement with conducting plates 199 and 201. Paddles 227 and 229 have respective associated handles 231 and 233, with corresponding defibrillating discharge control actuators 235 and 237. Placement of the paddles 227 and 229 on the plates 199 and 201 will depress the button actuators 205 and 207 to sound buzzer 221. Defibrillation may then be achieved by actuation of the discharge control buttons 235 and 237 to pass a defibrillating pulse through lines 165 and 167 to the electrode elements 31 and 33.

High voltage protection circuit 225 is illustrated as including series resistors 239 and 241, together with a spark-gap device 243 connected across the resistors. However, any appropriate type of high voltage protection circuit would be acceptable.

Impedance simulating network 223 is represented by the resistor 245. The permanent ECG cable 209 is also provided with a low pass filter network including resistor 247, capacitor 249 and oppositely poled diodes 251 and 253.

With either of the defibrillator cable 49 variations of FIG. 10 and FIG. 14, improved defibrillator operation is achieved. Among the improved features are the production of better current density distributions due to the provision of sufficient electrode area (electrode elements 31 and 33 are on the order of 8 cm. and 12 cm. in diameter, respectively), sufficient flexibility of the electrode elements to maximize the amount of available area that is in proximity to the skin of the patient, and the reduction of electrode element-to-skin impedance. Other advantages are that the electrodes 31 and 33 may be pre-applied to the patient and pre-connected to the defibrillator, so that a defibrillator pulse can be conveyed to the patient very shortly after the initiation of fibrillation. Also, use of disposable electrodes yields better control over the conductive medium or gel utilized, and the discharge control apparatus being located at a distance spaced from the patient provides better protection for the operator and other personnel.

Perhaps one of the most significant advantages of the present invention for defibrillation is that it permits utilization of a novel apex-posterior placement of the electrodes. The four schematic representations of FIG. 17 illustrate the advantages of this placement. In FIG. 17A the heart 255 is illustrated in its normal position nestled between the lungs 257 and 259. It is immediately obvious from this sketch that there are difficulties in getting sufficient defibrillating energy to the heart from the conventional sternum-apex placement of the defibrillating paddles 261 and 263. From the schematic diagram of FIG. 17B, the problem of getting sufficient defibrillating energy to the heart is dramatically clear. Not only is there significant energy loss directly between the paddles 261 and 263, but most of the current that reaches the heart is directed through only a portion thereof. Therefore, not only is it difficult to get energy to the heart, but the current that does not reach the heart is concentrated in a relatively small portion thereof and thus increases the risk of myocardial damage.

FIG. 17C demonstrates the novel apex-posterior placement utilized in connection with this invention. Thus, it may be seen that the smaller electrode element 31 is located in the apex or left leg position. There are two immediately obvious advantages of this placement. One is that the electrode is out of the way of any CPR efforts that may have to be performed on the patient. The other is that the electrode is located in a generally non-hairy portion of the body so that adherence and conductive problems are minimized. With the larger electrode element 33 located on the back in the right arm position, it is also in a generally non-hairy portion of the body and does not interfere with any operations that must be carried on from the front of the patient, as well as being spaced from the uneven spinal area. FIG. 17D dramatically illustrates how this positioning of the electrode elements 31 and 33 permits most of the defibrillating energy to be passed through the complete volume of the heart, with very minor interference by the lungs. Not only does this greater energy concentration in the heart increase the chances of successful defibrillation, but due to the distribution of this defibrillating energy over the entire heart the risk of myocardial damage is greatly lessened.

FIGS. 18 and 19 illustrate the combining of cables 49 and 51 to provide both the ECG monitoring and defibrillating functions through the single pair of electrode elements 31 and 33. When ECG electrode connector 87 is engaged with the ECG output terminal 147 on the defibrillator discharge control module 137, operation of the ECG 35 is just as if the connector 87 had been directly engaged with the connecting plug 45. The only difference is that an additional high voltage protection circuit 169 is provided to further protect ECG 35 from the high energy discharge pulses from the defibrillator 37. Further discussion of the details of these circuits would be repetitious, although it should be noted that the discharge control switches 157, 159, 161 and 163 are represented schematically in FIG. 19 by a single box 265 that may be termed the discharge control circuit.

By use of this combination, electrode elements 31 and 33 may be attached to a patient for monitoring by a separate ECG instrument 35. Of course, if the defibrillator 37 is the type that has an ECG built into the unit for monitoring through the defibrillating paddles, then the monitoring can occur without the use of the separate ECG 35 and cable 51. However, even with such a unit, it may be necessary to have a separate ECG or to be able to transmit the ECG signal to a remote location, such as a central hospital. The latter is particularly true of emergency situations, such as where a paramedic team is involved. Thus, the capability for connecting a separate ECG or a telemetry unit to the electrodes 31 and 33 through the ECG output connector 147 is very significant, as well as being extremely valuable in those cases where the defibrillator does not have a built-in ECG monitor.

If the ECG trace should indicate that the patient has gone into fibrillation, the electrode elements 31 and 33 are already in place for defibrillation, and these electrodes are already connected to the defibrillator through the cable 49. Thus, a defibrillating pulse may be applied to the patient almost as soon as it is noted that fibrillation is occurring, thereby increasing the chances of a successful conversion of the patient. Further, the action of the conducting gel on the skin increases the conductivity (and hence reduces the impedance) between the electrode element and the patient's body during an initial period after application of the electrode element. Therefore, by having the electrode elements pre-applied to the patient, the transmittal of defibrillating energy to the patient is improved. At the same time, nearly continuous ECG monitoring is achieved through the electrode elements 31 and 33, with the loss of the ECG trace for only a very minimal time during application of a defibrillating pulse. Therefore, this combination has great utility for paramedic use, for emergency room use, for operating room use and for intensive care use. Of course, it also has very significant utility in other types of situations, such as where a stimulating signal of another type is being applied to the body and it is desired to monitor the heart to be sure that the stimulation is not creating any cardiac problems.

In some situations, it may be desired to have only the ECG monitoring and defibrillating capacity, in which case the connecting plug 45 may have the pin arrangement illustrated in FIG. 20. From this schematic representation, it may be seen that the outer sheathes 55 are provided with female prongs 267 and 269, corresponding to the prongs 59 and 61 of the basic plug 45. However, the two middle sheathes contain solid non-conducting plugs 271 and 273.

An ESU cable 47' is illustrated in FIG. 21 and 22. A primed numeral is utilized to identify this cable, which does not include a cable connector that is included in the basic ESU cable 47, as discussed in more detail hereinafter. ESU cable 47' has an ESU instrument connector 275 at one end for connecting the cable to the ESU device. At the other end of cable 47' there is located an ESU electrode connector 277. ESU electrode connector 277 employs the same standardized rectangular box employed in the ECG and defibrillator electrode connectors 87 and 131.

With reference to FIG. 22, it may be seen that the ESU cable 47' includes a pair of conducting leads 279 and 281 that extend from the ESU instrument connector 275 to contacts 283 and 285 in the ESU electrode connector 277. Contacts 283 and 285 are capacitively coupled to another pair of contacts 287 and 289 in connector 277, such as by capacitors 291, 293 and 295. Although this preferred embodiment utilizes the two contacts 287 and 289, a single contact 287 could be employed, as discussed more fully hereinafter. If a single contact 287 were employed, the capacitive coupling would preferably extend to both of the leads 279 and 281, although only a single lead 279 could be used in some cases.

In some circumstances, the purchaser may only need or desire an ESU return pad for returning the RF current to the ESU instrument. For such a situation, a single ESU return pad 297 may be provided. Although any appropriate type of conductive pad could be employed, in this preferred embodiment an electrode element constructed in accordance with the discussion of FIG. 4, with the exception that just a conducting plate such as aluminum, rather than the tin-stannous chloride structure, is employed. For manufacturing simplicity, the ESU pad 297 may be identical to the electrode element 33 in other regards. As discussed above, there are many advantages to the particular ESU return pad of this invention, but certain aspects of the invention could also be utilized with other types of return pads.

ESU pad 297 is joined to a connecting plug 299 by one or more conducting lines. In this preferred embodiment, two conducting lines 301 and 303 are utilized. Plug 299 is essentially the same as plug 45, but with different pin placements (FIG. 25).

With reference to the circuit diagram of FIG. 24, it may be seen that the conducting lines 301 and 303 are connected to contacts 305 and 307, respectively, in the connecting plug 299. Two other contacts 309 and 311 in plug 299 are electrically connected or short circuited by a jumper or shorting bar 313.

When plug 299 is engaged with ESU electrode connector 277, conducting lines 301 and 303, and hence the ESU return pad 297, are capacitively coupled to the conducting leads 279 and 281 by the capacitors 291, 293 and 295. Actually, this capacitive coupling for the RF return could be accomplished with a single conducting line 301 and a single conducting lead 279 capacitively coupled by one or more of the capacitors 291, 293 or 295. For some ESU instruments this system would be perfectly acceptable. However, most ESU devices have a DC cord fault test circuit to ensure that an RF return path is established before the ESU may be energized. Thus, the preferred embodiment disclosed herein utilizes the two conducting leads 279 and 281 to provide a DC cord fault test circuit. This DC cord fault test loop is completed by the jumper 313 when contact 283 is electrically connected to contact 309 and contact 285 is electrically connected to contact 311. Of course, this cord fault test arrangement could be utilized with a single conducting line 301 capacitively coupled to the leads 279 and 281. However, for an additional safety margin, this preferred embodiment utilizes the second conducting line 303.

Capacitive coupling between the ESU return pad conducting lines 301 and 303 and the leads 279 and 281 is extremely important as a result of the DC and low frequency isolation that it provides. The most significant aspect of this isolation is the protection that it provides for the patient from low frequency or DC leakage from the ESU and from low frequency and DC signals being returned to the ESU as a result of rectification of RF signals during the electrosurgical process. In addition, the isolation provided by the capacitive coupling also protects the ESU instrument from high energy DC and low frequency signals, such as defibrillating pulses. Besides the capacitive coupling provided by the capacitors 291, 293 and 295, additional capacitive coupling may be provided on the connecting plug 299 side, such as by a capacitor 315 connected from one or both (with capacitive isolation) of the lines 301 and 303 to the jumper 313. As a matter of fact, all of the capacitive coupling could be located in the connecting plug 229, but safety and cost considerations favor at least some of this capacitive coupling being located in the ESU electrode connector 277.

Since the ESU return pad 297 would not suffice for ECG monitoring or defibrillation, it is necessary to ensure that the connecting plug 299 cannot engage a connector designed for ECG or defibrillation use. In this preferred embodiment, this is accomplished by the pin arrangement illustrated in FIG. 25 in which male prongs 317 and 319 correspond to the contacts 309 and 311 and female prongs 321 and 323 correspond to contacts 305 and 307.

FIGS. 26 and 27 illustrate the combination of an ECG 35 and an ESU 39 to provide the multiple functions of ECG monitoring and RF return to the ESU. The basic electrode set 53 is employed in this preferred embodiment, rather than the single ESU return pad. The same type of ESU instrument connector 275 is employed in connection with cable 47 as is used with cable 47'. An ESU electrode connector 325, rather than the ESU electrode connector 277, is utilized to engage the connecting plug 45. In addition, an ESU cable connector 327 has been added to provide for the connection of ECG cable 51 to the ESU cable 47. An ECG output terminal or connecting plug 329 having the same pin arrangement as plug 45 is located on the connector 327 to engage an ECG electrode connector 87.

In FIG. 27 it may been seen that the ECG electrode connector 87 has the body tissue impedance matching circuit 97, the high voltage protection circuit 99 and the low pass filter 101 of ECG cable 51. In addition, the ESU cable connector 327 includes another low pass filter 331 in association with the ECG output connector 329 in order to further protect the ECG from RF and sub harmonic interference. It may also be seen that a shorting jumper 333, corresponding to the jumper 313 in plug 299, is provided in plug 45. Although shorting jumper 333 is across the two center contacts, rather than two outer contacts as in plug 299, it performs the same function of providing a cord fault test loop with leads 279 and 281 when plug 45 and connector 325 are engaged. The same capacitive coupling may be provided in connector 325 that is provided in connector 277. In both cases, it should be recognized that the use of the capacitors 291, 293 and 295 is only illustrative and various other capacitor combinations may be utilized.

To provide a current path for the ECG signals and any other electrical signals passing through the ECG output connector 329, another pair of conducting leads 335 and 337 is provided in cable 47 between connectors 325 and 327. Leads 335 and 337 are connected to contacts in connector 335 that are electrically connected to the contacts in plug 45 connected to electrode elements 31 and 33 when plug 45 and connector 325 are engaged. At the other end, leads 335 and 337 are connected to ECG output terminal 329 through the low pass filter 331.

With the combination of FIGS. 26 and 27, it is possible to achieve continous ECG monitoring during an electrosurgical operation through the same electrode elements that are providing an RF return path. Since the ECG signals are obtained through the same electrode elements that are providing the RF return, the risk of RF burns occurring under the small ECG electrodes is eliminated. Also, the larger electrode element 33 is essentially the same as the ESU return pad 297, which works very effectively by itself. Thus, if so desired, capacitive coupling in connector 325 or plug 45 could be such as to utilize only the electrode 33 for the RF return. However, in the preferred embodiment disclosed herein, both electrode elements 33 and 31 are utilized for RF return, which provides even greater RF dispersion and further minimizes the risks of any RF burning. Thus, the addition of the electrode element 31 not only permits the utilization of a separate ECG 35 with the ESU 39, but it also provides a very efficient RF return system for the ESU.

With the assistance of the foregoing discussion, it is now possible to more fully comprehend the multiple function system of FIG. 1, as shown in greater detail in the schematic diagram of FIG. 28. One additional detail provided in this diagram is that the low pass filter 331 in ESU cable connector 327 is illustratively indicated as a capacitor 339 and a resistor 341 connected in parallel between the leads 335 and 337. Significant aspects of this circuit are that the capacitor 339 essentially isolates the ECG from the ESU RF signals or any other relatively high frequency interference, and the resistor 341 provides DC offset compensation as well as contributes to the filtering function.

It should also be noted that the numbers 291, 293 and 295 have been utilized to identify the capacitors in connector 325, thus corresponding them to the capacitors in connector 277, although the exact connections differ somewhat. Capacitor 295 is primarily a safety feature to ensure that the leads 279 and 281 are essentially short circuited for RF signals, although capacitors 291 and 293 would normally provide sufficient coupling for the RF signals. The contacts in connector 325 and plug 45 have not been separately identified, although they correspond to the contacts 283, 285, 287 and 289 in connector 277 (FIG. 24) and contacts 305, 307, 309 and 311 in plug 299 (FIG. 24). With reference to FIG. 3, it may be seen that the contacts 305 and 309 are actually the male prongs 63 and 65, between which the jumper 333 is connected. Also, the contacts 307 and 311 would correspond to the female prongs 59 and 61.

By utilizing the cables 47, 49 and 51, the ECG 35, the defibrillator 37 and the ESU 39 may be simultaneously connected to the electrode elements 31 and 33 to provide a multiplicity of functions through the single pair of electrode elements. Not only are a multiplicity of functions provided, but an improved physiological electrode system performance is achieved for each of the functions, if all of the features disclosed herein are utilized.

The significance of this multi-function capability of the single pair of electrode elements 31 and 33 may be illustrated by an example. In an emergency situation, paramedics would apply electrode elements 31 and 33 to the patient for ECG monitoring through an ECG cable 51 and a defibrillating cable 49, as illustrated in FIG. 18. If fibrillation of the patient's heart is observed, a defibrillating pulse of energy could be applied by depression of the discharge control module plungers 139, 141, 143 and 145. At the same time, ECG monitoring is nearly continuously maintained.

The patient is then conveyed to a hospital. If surgery is required, the patient is taken to the emergency room, where plug 45 may be disengaged from connector 131 of the paramedics' system and then engaged with a connector 325 in the system of FIG. 1. Thus, the same electrode elements 31 and 33 applied by the paramedics provide ECG monitoring, an RF return path for the ESU and the possibility of immediate defibrillation, if required.

After surgery, the patient could then be taken to the extensive care ward, where a system of cables 49 and 51 as shown in FIG. 18 could then be connected to electrode elements 31 and 33 for ECG monitoring. A defibrillator would not normally be attached to each patient, but when the onset of fibrillation was detected, a defibrillator could quickly be attached by the connector 129 to apply a defibrillating pulse to the patient. Alternatively, defibrillating cables 49 having a paddle converter 197 could be utilized, so that the defibrillating discharge could be effected through conditional paddles without the necessity of having to attach a connector 129 to the defibrillator.

Similarly, in an operating room the system of FIG. 1 could be attached to the patient for electrosurgery. After surgery, the patient could be transferred to the system of FIG. 18 in intensive care, as described above.

In another example, if the electrosurgery did not involve the cardiovascular structure and the ECG monitoring was merely precautionary, the system of FIG. 26 could be employed. If fibrillation were to unexpectedly occur, a defibrillator could be quickly connected to the ESU cable connector 327 to apply a defibrillating pulse through electrode elements 31 and 33.

In addition to the provision of a multiplicity of functions through a single pair of electrode elements, this invention also provides for the separate connection of each of the instruments to that pair of electrode elements. Further, each of the electrode elements itself involves a novel and improved form of physiological electrode, and the electrode elements are combined into an innovative disposable electrode set. Also, unique and novel cables are utilized to connect the electrode set to the various instruments. Therefore, this invention not only relates to the unique system, but it also relates to a number of novel and unobvious sub-systems and components of that physiological electrode system. Some of the unique features of these subsidiary portions of the system may also be used with other devices that are not directly a part of the physiological electrode system. Finally, the invention also includes certain alternative or partially modified variations.

While the preferred embodiments disclosed herein utilize the features shown and described, many of the innovative features of the invention disclosed could be utilized apart from the totality of features disclosed and hence would still fall within the spirit and scope of this invention. Therefore, although certain alternative and modified approaches or aspects have been disclosed herein, it also should be understood that various modifications, changes and variations may be made in the arrangement, operation and details of construction of the elements disclosed herein without departing from the spirit and scope of this invention.

I claim:

1. A disposable physiological electrode set adapted to be connected to a mating connector having two electrical lines for conveying monitoring signals or therapeutic energy from a patient, or for supplying stimulating or therapeutic energy to a patient, and two electrical lines joined to a DC cord fault tester, comprising:
   a first non-invasive electrode element to be attached to the skin of a patient;
   a second non-invasive electrode element to be attached to the skin of the patient, said first and second electrode elements constructed to have the characteristics required for monitoring, stimulating and therapeutic applications and comprising a non-conducting base member, a metal plate secured to said base, and a metal chloride affixed to said metal plate;
   connecting plug means to engage the mating connector and provide for the selective use of the electrode set for monitoring, stimulating or therapy, said plug means comprising four contacts in an electrically insulated housing, said plug means including means for electrically connecting the two electrical lines in said connector which are joined to the DC cord fault tester; and
   conducting means electrically connecting said first and second electrode elements to said plug means and the two electrical lines in the conductor which convey monitoring signals and therapeutic energy from the patient and which supply electrical energy for stimulation or therapy to the patient.

2. A disposable physiological electrode set adapted to be connected to a mating connector having two electrical lines for conveying monitoring signals or therapeutic energy from a patient, or for supplying stimulating or therapeutic energy to a patient, and two lines joined to a DC cord fault tester, comprising:
   a first electrode element;
   a second electrode element, said first and second electrode elements each comprising a non-conducting base member, a metal plate secured to said base, and a metal chloride affixed to said metal plate;
   a first electrically conducting line having one end thereof connected to said first electrode element;
   a second electrically conducting line having one end thereof connected to said second electrode element;
   a four-contact connecting plug means for engaging the mating connector and having four contacts in an electrically insulated housing, the other ends of said first and second conducting lines being connected to respective first and second contacts of said connecting plug means, which are adapted to mate with the two electrical lines in the connector which convey monitoring signals or supply stimulating or therapeutic energy; and
   electrically conducting means for interconnecting the third and fourth contacts of said connecting plug means, which are adapted to mate with the two electrical lines in the connector which are joined to the DC cord fault tester.

3. A disposable physiological electrode set as claimed in claim 2 and further comprising capacitive coupling means in said connecting plug means, said capacitive coupling means connected between one of said electrically conducting lines and said electrically conducting means.

4. A disposable physiological electrode set as claimed in claim 2 wherein each of said electrode elements comprises:
  and electrically conductive plate sufficiently thin to have enough flexibility to permit said conductive plate to substantially conform to the area of a patient's body to which it is attached;
  an electrically conductive medium to be located between said conductive plate and the skin of the patient to enhance electrical energy transfer between the patient and said conductive plate;
  an outer surface of said conductive plate being formed of an electrically conductive metal;
  a chloride of said electrically conductive metal affixed to said metal and located between said metal and said electrically conductive medium; and
  adhesive means for releasably attaching the disposable electrode element to the patient.

5. A disposable physiological electrode set as claimed in claim 4 wherein:
  said electrically conductive metal is tin; and
  said chloride is stannous chloride.

6. A disposable physiological electrode set comprising:
  connecting plug means providing for the selective use of the electrode set for monitoring, stimulating or therapeutic applications, said plug means having at least two contacts in an electrically insulated housing;
  first and second electrically conducting lines, each of said lines having a first end thereof secured to said two contacts of said connecting plug means; and
  first and second electrode elements to be attached to a patient, the second end of said first conducting line attached to said first electrode element and the second end of said second conducting line attached to said second electrode element wherein
  said first and second electrode elements each comprise a generally circular non-conductive base, a generally circular metal plate secured to said base, a metal chloride affixed to said metal plate, an electrically conductive medium secured in the electrode element between said metal plate and the patient, and adhesive means secured to the electrode element for attaching the electrode element to the patient, whereby when said electrode elements are attached to the patient a low impedance path is established from said lines to the patient's body through said electrode elements to provide a strong monitoring signal and minimal motion artifacts,
  at least one of said first and second electrode elements is sufficiently large to provide for the transfer of relatively high frequency energy between the patient's body and the electrode element with sufficient dispersion of the high frequency current to produce desirable current distribution and minimize the risks of skin burns,
  said first and second electrode elements are sufficiently large, and have a sufficiently low electrode element-to-skin impedance when attached to a patient, to maximize the transfer of a desired pattern of stimulating energy to the patient's body while minimizing the risk of skin burns, and
  said first and second electrode elements are capable of conducting high energy stimulating and therapeutic signals without loss of the desired characteristics thereof.

7. A disposable physiological electrode set as claimed in claim 6 wherein:
  said metal plate has at least a surface thereof formed primarily of tin; and
  said metal chloride is stannous chloride, a quantity of which is affixed to said tin between said tin and said electrically conductive medium.

* * * * *